US 6,576,263 B2
Jun. 10, 2003

(54) DELIVERY SYSTEMS USING PREFORMED BIODEGRADABLE POLYMER COMPOSITIONS AND METHODS

(75) Inventors: Myhanh T. Truong, Woodbury, MN (US); Kaveh Pournoor, St. Paul, MN (US); Hye-ok Choi, Woodbury, MN (US); David J. Velasquez, Cannon Falls, MN (US); Richard H. Ferber, Fridley, MN (US); Stephanie F. Bernatchez, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/784,934

(22) Filed: Feb. 16, 2001

(65) Prior Publication Data

US 2002/0009492 A1 Jan. 24, 2002

Related U.S. Application Data

(60) Provisional application No. 60/183,556, filed on Feb. 17, 2000.

(51) Int. Cl.[7] .................................................. A61K 9/14
(52) U.S. Cl. ....................... 424/489; 424/422; 424/423; 424/426; 424/484; 424/486; 424/499; 514/2; 514/772.1
(58) Field of Search ................................ 424/422, 423, 424/426, 484, 486, 489, 499; 514/2, 772.1

(56) References Cited

U.S. PATENT DOCUMENTS

| 4,101,380 A | 7/1978 | Rubinstein et al. |
|---|---|---|
| 4,250,163 A | 2/1981 | Nagai et al. |
| 4,349,530 A | 9/1982 | Royer .......................... 424/19 |
| 4,839,345 A | 6/1989 | Doi et al. |
| 4,897,268 A | 1/1990 | Tice et al. |
| 4,898,734 A | 2/1990 | Mathiowitz et al. |
| 4,919,939 A | 4/1990 | Baker |
| 4,976,968 A | 12/1990 | Steiner |
| 5,302,397 A | 4/1994 | Amsden et al. |
| 5,470,582 A | 11/1995 | Supersaxo et al. |
| 5,508,060 A | 4/1996 | Perman et al. |
| 5,512,268 A | * 4/1996 | Grinstaff et al. ......... 424/9.322 |
| 5,583,114 A | 12/1996 | Barrows et al. |
| 5,700,476 A | 12/1997 | Rosenthal et al. |
| 5,733,563 A | 3/1998 | Fortier |
| 5,759,563 A | 6/1998 | Yewey et al. |

FOREIGN PATENT DOCUMENTS

| WO | WO 90/13540 | 11/1990 |
|---|---|---|
| WO | WO 93/00076 | 1/1993 |
| WO | WO 96/03159 | 2/1996 |
| WO | WO 99/66964 | 12/1999 |

OTHER PUBLICATIONS

Weissleder, R. et al., "Quantitation of Slow Drug Release from an Implantable and Degradable Gentamicin Conjugate by In Vivo Magnetic Resonance Imaging," *Antimicrobial Agents and Chemotherapy, American Society for Microbiology*, vol. 39, No. 4, Apr. 1995, pp. 839–845.

Bernatchez et al., "Sodium hyaluronate as a vehicle for an improved tolerance of 5–fluorouracil administered subconjunctivally to rabbits," *International Journal of Pharmaceutics*, 106, pp. 161–166 (1994).

(List continued on next page.)

Primary Examiner—Thurman K. Page
Assistant Examiner—Liliana Di Nola-Baron
(74) Attorney, Agent, or Firm—Christopher D. Gram; John A. Burtis

(57) ABSTRACT

A preformed object for delivering an active agent for a subject, the preformed object including crosslinked protein, and methods of making and using.

28 Claims, 12 Drawing Sheets

OTHER PUBLICATIONS

Liang et al., High–performance liquid chromatographic assay of cefazolin in rat tissues, *Journal of Chromatography B: Biomedical Applications*, 656, pp. 460–465 (1994).

Mathiowitz et al., "Bioadhesive Drug Delivery Systems," *Encyclopedia of Controlled Drug Delivery*, vol. 1, pp. 9–45 (1999).

Bromberg et al., "Temperature–responsive gels and thermogelling polymer matrices for protein and peptide delivery," *Advanced Drug Delivery Reviews*, vol. 31, pp. 197–221 (1998).

Pendharkar et al., "Development of an Albumin Based Lung Sealant," *Society for Biomaterials*, Sixth World Biomaterials Congress Transactions, p. 316 (2000).

Blum et al., "Effect of Material Composition on Shear Strength of an Adhesive Albumin," *Society for Biomaterials*, Sixth World Biomaterials Congress Transactions, p. 106 (2000).

D'Urso et al., "New Hydrogel Based on Polyethylene Glycol Cross–Linked With Bovine Serum Albumin," *Biotechnology Techniques*, vol. 8, No. 2, pp. 71–76 (1994).

Quirk et al., "Production of Recombinant Human Serum Albumin from *Saccharomyces cerevisiae*," *Biotechnology and Applied Biochemistry*, 11, 273–287 (1989).

Kalman et al., "Synthesis of a gene for human serum albumin and its expression in *Saccharomyces cerevisiae*," *Nucleic Acids Research*, vol. 18, No. 20, pp. 6075–6081 (1990).

Sleep et al., "The Secretion of Human Serum Albumin From the Yeast *Saccharomyces Cerevisiae* Using Five Different Leader Sequences," *Bio/Technology*, vol. 8, pp. 42–46 (1990).

Sijmons et al., "Production of Correctly Processed Human Serum Albumin in Transgenic Plants," *Bio/Technology*, vol. 8, 217–221 (1990).

Abuchowski et al., "Cancer Therapy With Chemically Modified Enzymes," *Cancer Biochem. Biophys.*, vol. 7, pp. 175–186 (1984).

Ranade et al., "Role of Polymers in Drug Delivery," *Drug Delivery Systems*, CRC Press, Inc., Boca Raton, FL, pp. 78–81 (1996).

* cited by examiner

DELIVERY SYSTEMS USING PREFORMED BIODEGRADABLE POLYMER COMPOSITIONS AND METHODS

This application claims priority from U.S. Provisional Application Ser. No. 60/183,556, filed on Feb. 17, 2000.

BACKGROUND

A variety of approaches have been developed to permit the delivery of an active agent, such as a drug, to a subject, preferably for the sustained release of such agent. Such delivery systems are typically designed to protect the agent from the environment prior to delivery while permitting the controlled release of the agent to the targeted area of the subject.

A number of conventional controlled release systems are based on microstructures, such as liposomes, liposphers, microcapsules, microparticles, and nanoparticles, as well as macrostructures, such as cylinders, discs, and fibers. Typically, an active agent, such as a drug, is blended with a polymer and then formed into the desired shape.

Many of such conventional systems cannot be used to form a solid implant with the structural integrity required for prosthetic applications. Furthermore, many of such systems cannot be used to form articles that can be infused with an active agent (e.g., drug) by a physician, for example, at the time of application to the subject. Also, many of such systems include polymers that cannot be easily controlled with respect to the rate of biodegradation and/or the rate of release of any incorporated active agents.

Hydrogels (e.g., a class of polymers that are swollen in an aqueous medium but do not dissolve in water) made by the crosslinking of albumin with polyethylene glycol (PEG) derivatives have been studied previously for possible drug delivery applications (D'Urso et al., *Biotech. Tech.*, 8, 71–76 (1994)). Another approach to the controlled delivery of drugs involves microencapsulation or microsphere formation with the use of synthetic bioabsorbable polymers such as poly(lactic acid) and various copolymers of lactide and glycolide. A drawback to the use of microspheres, however, is that they cannot be coated evenly and retained on the surface of a surgical site or on injured or diseased tissue. To address this problem, microsphere-containing membranes have been made by suspending the microspheres in a solution of a second polymer made with the use of a solvent that is a nonsolvent for the microspheres and then casting a film out of the mixture.

Thus, there is a need for other delivery systems, particularly for one that includes a polymer composition that can be varied to provide a range of biodegradation rates and delivery rates. Preferably, there is a need for a delivery system that includes a polymer composition that has sufficient structural integrity to be easy to handle.

SUMMARY

The present invention provides a preformed object for delivering an active agent to a subject, the preformed object being at least partially desolvated crosslinked albumin having a crosslinking agent of the formula:

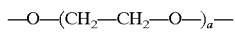

wherein:
X is a difunctional polyoxyethylene chain portion or a bond;
LM is a difunctional linking moiety represented by the formulas —C(O)—, —(CH$_2$)$_b$C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments;
G is a leaving group selected from the group of N-oxysuccinimidyl, N-oxymaleimidyl, N-oxyphthalimidyl, nitrophenoxyl, N-oxyimidazolyl, and tresyl;
I is a multifunctional linking moiety derived from a multinucleophilic compound; and
n is an integer from 2 to 10;
with the proviso that when X is a difunctional polyoxyethylene chain portion —X—I—X— is PEG, which is a diradical fragment represented by the formula:

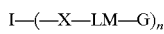

wherein a is an integer from 20 to 300.

Other embodiments of the present invention include such preformed objects with an active agent incorporated therein, which may or may not be resolvated, and such preformed objects having an active agent therein further incorporated into a secondary biodegradable matrix. Other embodiments include preformed objects of other biodegradable polymers having an active agent therein further incorporated into a secondary biodegradable matrix, which is of the chemistry described above for the preformed objects. Methods of making and methods of delivering an active agent to a subject are also provided by the present invention.

DETAILED DESCRIPTION OF PREFERRED EMBODIMENTS

Figure 1:
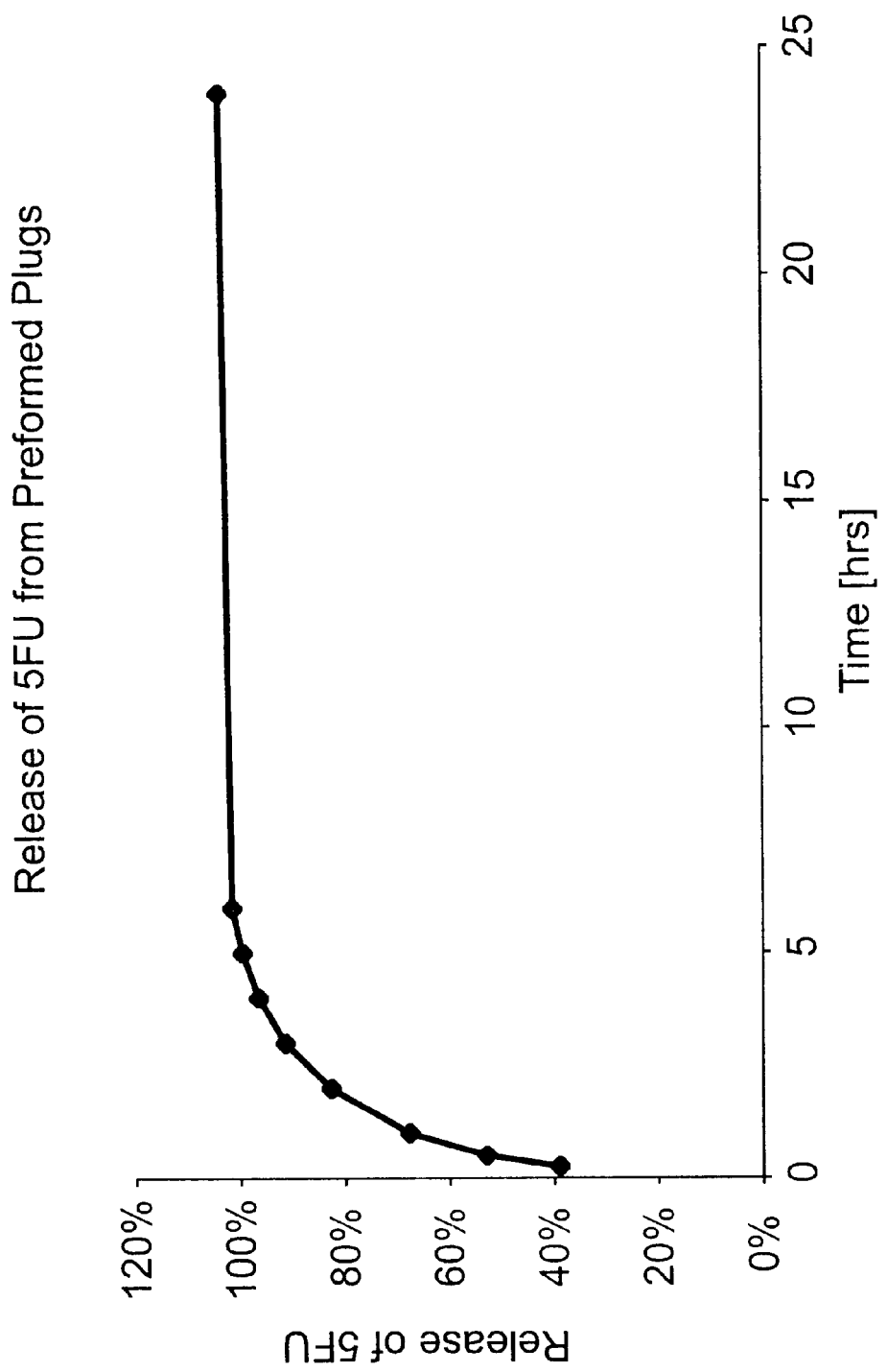
FIG. 1 shows the release of 5-fluorouracil (5-FU) from preformed plugs of albumin crosslinked with PEG-(SS)$_2$ crosslinker.

The present invention provides preformed objects, preferably preformed, self-supporting objects, that include a first biodegradable composition and optionally an active agent, such as a drug, for delivery to a targeted area of a subject. The preformed objects can be at least partially desolvated (e.g., at least partially dehydrated) and subsequently combined with an active agent, or the active agent can be included at the time of preparation of the preformed objects. Such preformed objects are preferably prepared from a biodegradable composition that is used conventionally to bond or seal tissue by applying the starting materials (e.g., protein and crosslinking agent) to tissue and curing (e.g., crosslinking) in the presence of the tissue of the subject. Herein, however, preferred objects are prepared from the same or a similar composition, cured (e.g., crosslinked), and then applied to the tissue of the subject. Thus, there is typically no bonding interaction between the preformed objects and the tissue.

Preferred preformed objects of the present invention have sufficient structural integrity to maintain their general shape and be self-supporting once formed (e.g., cured), as long as they are stored under appropriate conditions (e.g., in the absence of moisture if desolvated or at a temperature of about 4° C. if solvated). The degree of mechanical strength, flexibility, cure rate, and biodegradation rate can be varied depending on the choice of components used to make the preformed objects. Preferred preformed objects of the present invention include a crosslinked protein. They are typically prepared from a buffered basic protein solution and a multifunctional, and typically a difunctional, crosslinking agent. The buffered protein solution and the crosslinking agent are typically obtained using commercially available materials, which provides benefit because most of these materials generally have a history of clinical safety and/or use.

Suitable proteins for use in the present composition include nonimmunogenic, water soluble proteins, preferably albumin (more preferably serum albumin, and most preferably, human serum albumin). A preferred buffered protein solution that may be used to prepare the preformed objects of the present invention include concentrated aqueous serum albumin, buffered to a pH of about 8.0 to about 11.0, where the buffer concentration is in a range of about 0.01 molar to about 0.25 molar. Suitable buffer systems include buffers which are physiologically and/or clinically acceptable such as known carbonate or phosphate buffer systems, provided the buffer does not adversely react with or otherwise alter the crosslinking agent. A preferred buffer system is a carbonate/bicarbonate buffer system at a pH value of about 9.0 to about 10.5 at a concentration in the range of about 0.05 to about 0.15 molar.

Serum albumin is readily isolated from serum using known isolation processes. In addition, it is possible to produce albumin from genetically transformed cells. See, for example, the reports of Quirk et al., *Biotechnology and Applied Biochemistry*, 11, 273–287 (1989), Kalman et al., *Nucleic Acids Research*, 18, 6075–6081 (1990), Sleep et al., *Biotechnology*, 8, 42–46 (1990), and Sijmons et al., *Biotechnology*, 8, 217–221 (1990). The ability to produce recombinant albumin provides the benefit that protein produced by this method will be free of human pathogens, viruses or other contaminants that might contaminate albumin that is isolated directly from human serum.

When used in the present buffered mixtures it has been found that the serum albumin is not denatured. Because the albumin is not denatured before it is used it is believed that the albumin retains its natural, coiled conformation and thus, after being crosslinked during the curing process to provide a gel-like solid, the cured preformed objects retain sufficient flexibility to provide a suitable matrix for implantation if desired.

A variety of suitable crosslinking agents may be used in the present invention. The crosslinking agents are multifunctional, and preferably difunctional. Suitable crosslinking agents for use in the present invention include compounds of the formula:

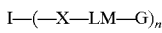

wherein X is a difunctional polyoxyethylene chain portion or a bond, LM is a difunctional linking moiety, G is an activated leaving group, I is a multifunctional linking moiety derived from a multinucleophilic compound (e.g., ethylene glycol, pentaerthritol, trymethylol propane, multinucleophilic amines, etc.), and n is about 2 to about 10, preferably about 2 to about 4, with the proviso that when X is a difunctional polyoxyethylene chain portion "—X—I—X—" is -PEG- as defined herein.

Preferred crosslinking agents are difunctional and have the formula:

in which —PEG— is a diradical fragment represented by the formula

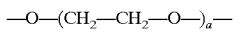

where a is an integer of about 20 to about 300; —LM— is a diradical fragment represented by the formulas —C(O)—, —(CH$_2$)$_b$C(O)— where b is an integer of about 1 to about 5, —C(O)—(CH$_2$)$_c$—C(O)— where c is an integer of about 2 to about 10 and where the aliphatic portion of the radical may be saturated or unsaturated, —C(O)—O—(CH$_2$)$_d$—O—C(O)— where d is an integer of about 2 to about 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer of about 2 to about 10, d is an integer of about 2 to about 10, and R is a polymer or copolymer having 1 to 10 monomeric lactide, glycolide, trimethylene carbonate, caprolactone or p-dioxanone fragments; and -G is a leaving group such as a succinimidyl, maleimidyl, phthalimidyl, nitrophenyl, imidazolyl, or tresyl leaving group. In the context of a leaving group, "succinimidyl" means N-oxysuccinimidyl, "maleimidyl" means N-oxymaleimidyl, "phthalimidyl" means N-oxyphthalimidyl, "nitrophenyl" means nitrophenoxyl, "imidazolyl" means N-oxyimidazolyl, and "tresyl" means (CF$_3$—CH$_2$—SO$_2$—O—).

The -PEG- portion of the crosslinking agent is preferably derived from commercially available compounds having a weight average molecular weight of about 1,000 to about 15,000, preferably having a weight average molecular weight of about 2,000 to about 4,000. These compounds have been used in different types of biomedical materials because they have been demonstrated to be nontoxic as well as rapidly excreted from the body when the molecular weight is below about 30,000.

The leaving group, -G, portion of the crosslinking agent is an activated leaving group which allows the crosslinking agent to react or chemically bind to free primary or secondary amine groups of a protein. Suitable leaving groups include N-oxysuccinimidyl, other imides such as N-oxymaleimidyl and N-oxyphthalimidyl, heterocyclic leaving groups such as N-oxyimidazolyl, aromatic leaving groups such as a nitrophenoxyl, or fluorinated alkylsulfone leaving groups such as tresyl ($CF_3$—$CH_2$—$SO_2$—O—). A preferred leaving group is the N-oxysuccinimidyl group because studies of the mutagenicity, oncogenicity and teratogenicity of this group suggest that the small amount of this leaving group does not present a local or systemic toxicology risk.

The crosslinking agents may be prepared using known processes, procedures or synthetic methods such as the procedures reported in U.S. Pat. Nos. 4,101,380 or 4,839,345, the procedure reported in International Application Ser. No. PCT/US90/02133 filed Apr. 19, 1990 or the procedure reported by Abuchowski et al., *Cancer Biochem. Biophys.*, 7, 175–186 (1984). Briefly, polyethylene glycol and a suitable acid anhydride are dissolved in a suitable polar organic solvent in the presence of base and refluxed for a period of time sufficient to form a polyethylene glycol diester diacid. The diester diacid is then reacted with a leaving group such as an N-hydroxy imide compound in a suitable polar organic solvent in the presence of dicyclohexylcarbodiimide or other condensing agents and stirred at room temperature to form the desired difunctional crosslinking agent.

Alternatively, polyethylene glycol and a suitable dicarboxylic acid chloride or bischloroformate may be dissolved in a suitable polar organic solvent for a period of time sufficient to form the mixed acid chloride polyethylene glycol ester or mixed chloroformate polyethylene glycol ester. The mixed esters may then be reacted with a compound such as an N-hydroxy imide compound in a suitable polar organic solvent and stirred at an elevated temperature for a period of time sufficient to form the desired difunctional crosslinking agent.

The preformed objects may be prepared using conventional methods of crosslinking materials, such as proteins, and conventional methods of forming crosslinked polymers into shapes, such as beads or microspheres, including extrusion techniques, spray drying techniques, and emulsion polymerization techniques. Such methods are well known to those of skill in the art of polymer chemistry.

One may tailor the cure time of the present compositions by using buffers having different pH values to modify the protein pH. For example, by varying the pH of the buffer it is possible to modify the pH of the albumin and thus change the cure rate time from about 10 seconds to less than about 10 minutes. Briefly, mixing concentrated aqueous serum albumin at higher pH with the crosslinking agent provides the fastest cure times. It has also been found that higher concentrations of protein and crosslinking agent provide a relatively stronger, cured matrix. However, if the mixtures are too concentrated and viscosity becomes too great, the resulting cured matrix becomes weak and globular. In addition, if the concentration of crosslinking agent is too high, the resulting cured matrix may swell to such an extent that the strength of the matrix in the presence of water or other fluids is lowered.

Compositions that are used to form the preformed objects of the present invention are described in U.S. Pat. No. 5,583,114 (Barrows et al.). Therein, however, the compositions are applied directly to tissue and cured in situ to create a bonding interaction with the tissue. They are used, for example, to eliminate or substantially reduce the number of sutures normally required using current practices, to attach skin grafts and to position tissue flaps or free flaps during reconstructive surgery, to close gingival flaps in periodontal surgery. In all of these applications, the compositions form a thin layer of cured adhesive that is effectively sandwiched between two adjacent layers of living tissues. Alternatively, the compositions are disclosed as being used as a sealant, for example, to prevent air leaks associated with pulmonary surgery or to inhibit or prevent bleeding in other surgical procedures. When used in this manner, the underlying tissue may be coated with a relatively thick layer of adhesive.

In contrast, the compositions described herein are shaped into objects prior to contacting the subject. Thus, the term "preformed" refers to providing a form or shape to the polymeric composition prior to contacting a subject with the object. Preferably, the preformed objects have a 3-dimensional shape that is self supporting. Thus, such preformed objects do not include thin films or layers; however, if the shape is in that of a sheet material or layer on a backing to form a patch, for example, the preformed object has a thickness of greater than about 2 millimeters. The preformed objects of the present invention can be in the form of microstructures, such as microcapsules, microparticles, nanoparticles, and the like, as well as macrostructures, such as beads or other ball-shaped objects, cylinders, discs, fibers, sheets, plugs, ribbons, wedges, and the like. Preferred structures are microspheres and beads. Typically, the beads have a diameter of greater than about 1 millimeter and the microspheres have a diameter of about 1 micron to about 1000 microns.

The preformed objects can be at least partially desolvated, and preferably substantially completely desolvated, after formation. Herein, "desolvated" means that the solvent used during preparation is removed from the preformed object subsequent to reaction between the protein and the crosslinker. Typically, this means that the preformed objects are at least partially dehydrated due to the removal of at least part of the water incorporated into the preformed objects upon their initial formation. Other solvents can be used besides, or in addition to, water during the preparation of such preformed objects. Significantly, preferred preformed objects of the present invention retain their shape upon desolvation and resolvation.

Once the preformed objects are at least partially desolvated, it is desirable to store them in an environment that does not allow resolvation due to atmospheric moisture, for example. Such objects are desirable because they are easy to handle and can be provided to a physician and resolvated with an active agent at the time of use.

Whether desolvated or not, the preformed objects can include an active agent. Preferred embodiments of the preformed objects of the present invention include an active agent incorporated therein. As used herein, an "active agent" is one that is capable of producing a desired effect, whether it be chemically, pharmacologically, physically, or biologically. Thus, a resultant preformed object with one or more active agents incorporated therein can function as a delivery system for drugs, medicaments, or other active agents. The preformed objects can be placed in contact with tissue, such as when implanted into a body cavity or tissue void, for example, in a subject, or on the outside of a subject, as on the skin, for example.

The active agent can be added during formation of the preformed object, e.g., during reaction of the protein and crosslinker, or subsequent thereto. If the active agent is incorporated into the preformed object during formation, it is preferred that the active agent does not react with either the crosslinking agent or the protein. For certain preferred embodiments, the active agent is combined with the preformed, at least partially desolvated, object with a liquid that is or includes an active agent to form a resolvated preformed object with the active agent incorporated therein. This resolvated, preformed object can then be placed in contact with the subject for delivery of the active agent. Specific methods of incorporating active agents into the preformed objects, either during their formation or subsequent thereto, are disclosed in the examples below.

In one aspect of the present invention, this involves resolvating a plurality of ball-shaped preformed objects with an aqueous composition containing an active agent, such as an antibacterial agent, and packing the plurality of such objects into a tissue void, such as an abscess or debrided bone cavity. Thus, in one particular embodiment, resolvated preformed objects containing an antibacterial agent can be used in the treatment of osteomyelitis. Osteomyelitis is an infection of the bone and its marrow and results in the formation of bone lesions. The etiologic agent is usually staphylococci. It is a difficult infection to treat and eradicate. The current practice is long-term prophylactic antibiotics with multiple surgical debridements. Following debridement surgery, the dead space created by osteomyelitic tissue removal is packed with polymethylmethacrylate bone cement beads, which are not biodegradable. Although such beads are a proven carrier of antibiotics, they are less than ideal as they do not degrade in vivo and can result in tissue incompatibility reactions. Thus, the preformed objects of the present invention containing one or more antibiotics can be used in the treatment of osteomyelitis.

Significantly, the rate of biodegradation of the preformed objects can be tailored for a desired use by the choice of protein, crosslinker, and the conditions of the preparation. As used herein, "biodegradation" refers to the conversion of the preformed objects into less complex intermediate or end-products by a variety of mechanisms, including solubilization, hydrolysis, enzymatic, and the action of biological entities, which leads to a decrease in the integrity of the material. The polymer molecules can, but need not necessarily, break down into smaller fragments. Such biodegradation includes within its scope bioresorption, bioabsorption, or bioerosion of the preformed objects. Typically, preformed objects of the present invention can be formulated to degrade over a period of about 2 days to about 60 days.

Release of the active agent typically occurs by a combination of erosion of the polymer and diffusion of the active agent out of the polymer. The diffusion component may or may not follow Fick's Law, while erosion contribution follows the kinetics of degradation. The rate of release of the active agent can be tailored to be within a range of about several hours to several months, typically, up to about 60 days.

The active agent can be selected from a wide variety of agents that provide physiological, pharmacological, or biological effect, which may be therapeutic or prophylactic, for example. Examples include a substance, or metabolic precursor thereof, that can enhance cell growth, enhance tissue regeneration, enhance angiogenesis and vascularization, enhance nerve stimulation, enhance bone growth, inhibit (e.g., prevent, reduce, or reverse) infection (e.g., bacterial or viral) and/or inflammation, inhibit cancer cell growth (e.g., treat an existing malignant condition or prevent the conversion of a premalignant condition to a malignant condition), modify the immune response, promote wound healing, or promote tissue softening and moisturizing. Such substances include, but are not limited to: antibacterials, such as tetracycline, vancomycin, and cephalosporins; growth factors, such as platelet-derived growth factor, transforming growth factor beta, epithelial growth factor, and fibroblast growth factor; anticancer (e.g., antimitotic) agents, such as 5-fluorouracyl, mitomycin, methotrexate, doxorubicin, and cisplatins; local anesthetics, such as lidocaine, bupivacaine, tetracaine, procaine, and prilocaine; antiseptics (e.g., chlorhexidine); hormones (e.g., steroids, insulin); antiviral agents; narcotic antagonists; immune response modifiers; ocular drugs (e.g., atropine, pilocarpine, and timolol); vaccines; and cosmeceuticals. Other specific examples are listed in U.S. Pat. No. 5,733,563 (Fortier et al.) and U.S. Pat. No. 5,759,563 (Yewey et al.). One or more of such active agents may be incorporated into the preformed objects of the present invention.

Preformed objects of the present invention, preferably having an active agent incorporated therein, can be incorporated into a secondary biodegradable matrix. This secondary biodegradable matrix may be applied to a subject as a liquid (e.g., microspheres within a liquid) or it can be formed into a shaped object (e.g., preformed shaped objects such as microspheres within a shaped object). Thus, the preformed objects can be incorporated into the matrix for delivery to a subject. The secondary biodegradable matrix can be of the same chemistry as that of the preformed objects, preferably as described above and in U.S. Pat. No. 5,583,114 (Barrows et al.), or it can be of another biodegradable polymer. Similarly, the preformed objects include the crosslinked protein described above, or they can be of another biodegradable polymer. Examples of suitable biodegradable polymers for either the matrix or the preformed objects includes those disclosed in *Drug Delivery Systems*, V. V. Ranade, ed., CRC Press, Inc., Boca Raton, Fla., pages 78–81, 1996, and *Biodegradable Polymers as Drug Delivery Systems*, M. Chasin, ed., Volume 45 of Drugs and the Pharmaceutical Sciences Series, Marcel Dekker, Inc., N.Y. 1990. Preferred examples of the secondary biodegradable matrix include poly(phosphoesters), poly(alpha-hydroxy acids), hydrophilic acrylate and methacrylate polymers, hydroxyproline polyesters, polyanhydrides (e.g., poly(lactide-co-glycolide)), polycaprolactones, poly(ortho esters), polyphosphazenes, poly(amino acids), polysaccharides, and copolymers thereof. Preferred examples of the preformed objects include poly(alpha-hydroxy acid)s (e.g., poly(glycolic acid), poly(DL-lactic acid) and poly(L-lactic acid)), poly(amino acids), poly(anhydrides), poly(orthoesters), poly(phosphazines), poly(phosphoesters), polylactones (e.g., poly(epsilon-caprolactone), poly(delta-valerolactone) and poly(gamma-butyrolactone). The preformed objects can be incorporated into the secondary biodegradable matrix using techniques known to one of skill in the art. For example, the tissue sealant disclosed in U.S. Pat. No. 5,583,114 (Barrows et al.) can be used as a secondary biodegradable matrix to deliver preformed objects incorporated therein to a subject.

Objects and advantages of this invention are further illustrated by the following examples, but the particular materials and amounts thereof recited in these examples, as well as other conditions and details, should not be construed to unduly limit this invention.

EXAMPLES

Preparation of Albumin Solution

Albumin was obtained as human serum albumin at 25% concentration from Baxter Healthcare (Deerfield, Ill.). It was either processed by dialysis (Procedure A) as described in U.S. Pat. No. 5,583,114 (Barrows et al) or was processed by continuous diafiltration (Procedure B) using a MINIKROS Sampler Lab Unit for tangential flow separations (available from Spectrum Laboratories, Inc., Rancho Domingues, Calif.) equipped with a 680 cm² polysulfone fiber module with a 50,000 molecular weight cutoff (also available from Spectrum Laboratories, Inc.). The albumin obtained from the Barrows process (U.S. Pat. No. 5,582,114) (Process A) was diluted to a 23% solution using a 0.1M carbonate/bicarbonate buffer solution at pH 10. In the case of the albumin obtained by diafiltration (Process B), the diafiltration was done with a 0.075M carbonate/bicarbonate buffer at pH 8.9–9.1. The sample was concentrated to 29%–30% using the diafiltration equipment. The final concentration of albumin was determined by standard biuret titration. Synthesis of Polyethylene Glycol Disuccinimidyl Succinate $(PEG-SS)_2$ Crosslinker A 30 gallon glass-lined reactor was charged with 10.9 kg polyethylene glycol (3400 molecular weight), 760 grams of succinic anhydride and 4.4 kg toluene. The charges were mixed at 110 deg C. under a nitrogen blanket for 6 hours. The reaction mixture was then cooled to 80 deg C. 13.0 kg absolute ethanol was added, with stirring. No additional heat was added. The mixture was stirred until the temperature cooled to 25 deg C. 43.8 kg methyl tert-butyl ether (MtBE) was added to the cooled mixture with stirring and mixed under a nitrogen atmosphere overnight. The reaction mixture was centrifuged. The reactor was rinsed with four additional portions of MtBE. This rinse was used to wash the centrifuge cake. The filter cake of polyethylene glycol disuccinate was dried at 30 deg C. under a vacuum in a blender dryer for approximately 19.5 hours. 10.9 kg of polyethylene glycol disuccinate was recovered.

A 30 gallon glass-lined reactor was charged with 5.6 kg polyethylene glycol disuccinate, 540 grams N-hydroxysuccinimide, 84 grams of 4-dimethylaminopyridine and 8.2 kg acetonitrile. The charges were mixed for 1 hour at room temperature until all solids were dissolved. 1.3 kg 1-ethyl-3-(3-dimethylaminopropyl)carbodiimde were added. The mixture was stirred at 25 deg C. under a nitrogen blanket for 6 hours. Then 39.6 kg absolute ethanol was added to the reaction mixture with stirring. The mixture was transferred to a 75 gallon portable glass-lined reactor. 80.0 kg of MtBE was added with stirring. The mixture was stirred overnight with cooling on the jacket. The reaction mixture was at 5–7 deg C. the next morning. The reaction mixture was centrifuged and the reaction flask was rinsed with four parts of MtBE. This rinse was used to wash the centrifuge cake. The centrifuged wet cake was added to a 30 gallon glass-lined reactor along with 40 kg absolute ethanol. The reactor was mixed for approximately 1 hour at ambient temperature under a nitrogen atmosphere. The mixture was centrifuged, the reactor was rinsed with 40 kg absolute ethanol and this rinse was used to wash the centrifuge cake. The reactor was then rinsed with 40 kg MtBE and this rinse was used to wash the centrifuge cake. Approximately half of the cake was transferred to a tumble dryer and was dried approximately 18 hours at 30 deg C. under vacuum. 2.7 kg of the dried product was milled using liquid nitrogen cooling. 2.55 kg of polyethylene glycol disuccinimidyl succinate, $PEG-(SS)_2$ was recovered from each half of the cake.

Example 1

Release of 5-Fluorouracil (5FU) from Preformed Albumin Polymer Plug

Two polymer plugs were preformed in a modified 5-milliliter (ml) poly syringe, wherein the syringe barrel was cut to form an open cylindrical receptacle, and then by mixing 0.5 ml of 29% albumin solution (obtained from American Biological Technology, Seguin, Tex. or by diafiltration (Procedure B) as described above) and 0.5 ml of 136 mg/ml $PEG-(SS)_2$ crosslinker. After crosslinking was complete (15 minutes) the plugs were removed from the syringe and pushed out. The polymer plugs were dried under vacuum for 24 hours (hr). The plugs were reconstituted with 2 ml of a 5FU solution (1.04 mg/ml from Sigma Chemical Co, St. Louis, Mo.) so that each plug contained a total of 187.6 micrograms ($\mu$g), or 165.5 $\mu$g of 5FU. Each plug was placed into a separate vial, and five ml of phosphate buffered saline (PBS), at pH 7.4, were added at sample time 0 ($t_0$). The vials were maintained at room temperature and were shaken continuously. At each sample time, the entire content of the vial was removed and replaced with 5 ml of fresh PBS. Samples were taken at 0.25 hr, 0.5 hr, 1 hr, 2 hr, 3 hr, 4 hr, 5 hr, 6 hr, and 24 hr. Ana of 5FU was analyzed by high-pressure liquid chromatography, following the method of Bernatchez et al., *Int. J. Pharm.*, 106, 161–166 (1994). The data in FIG. 1 show that the 5FU was released over a 5 hr time period.

Example 2

Release of Tetracycline from Biopolymer Plug

Alginic acid (30 mg, Sigma Chemical Co., St. Louis, Mo.) was added to 1 ml of 1.01 mg/ml tetracycline (Sigma Chemical Co., St. Louis, Mo.). The pH of the mixture was brought to 6.8 with 1 N NaOH using CloropHast pH strips (Fischer Company, Itaska Ill.), and then placed into a vacuum desiccator with DRIERITE (W.A. Hammond Drierite Co., Xenia, Ohio) to dry for 24 hr. The resulting alginate/tetracycline film was ground up and mixed into the 30% albumin solution (Procedure B) just prior to being placed into 5 ml poly syringe forms and crosslinked with an equivalent volume of $PEG-(SS)_2$ crosslinker (136 mg/ml). Each plug was placed into a separate vial, and five ml of phosphate buffered saline (PBS), at pH 7.4, were added at sample time 0 ($t_0$). The vials were maintained at room temperature and were shaken continuously. At each sample time, the entire content of the vial was removed and replaced with 5 ml of fresh PBS. Samples were taken at 1 hr, 2 hr, 3 hr, 5 hr, and 24 hr. The samples were analyzed on a Hewlett Packard (Palo Alto, Calif.) HPLC model 1190 with a variable wavelength detector, and a reverse phase, LC-8-DB column (15.0 cm×4.6 mm, 5 micron particle size) from Supelco Co. (Bellefonte, Pa.). The mobile phase used for HPLC analysis consisted of 0.05 M ammonium phosphate buffer (pH 6.8), methanol, acetonitrile, and triethylamine in the ratio of 45:45:10:1. The flow rate of the mobile phase was 1.0 ml/minute, and the column temperature was maintained at 25° C. Tetracycline was detectable at 280 nm.

Figure 2:
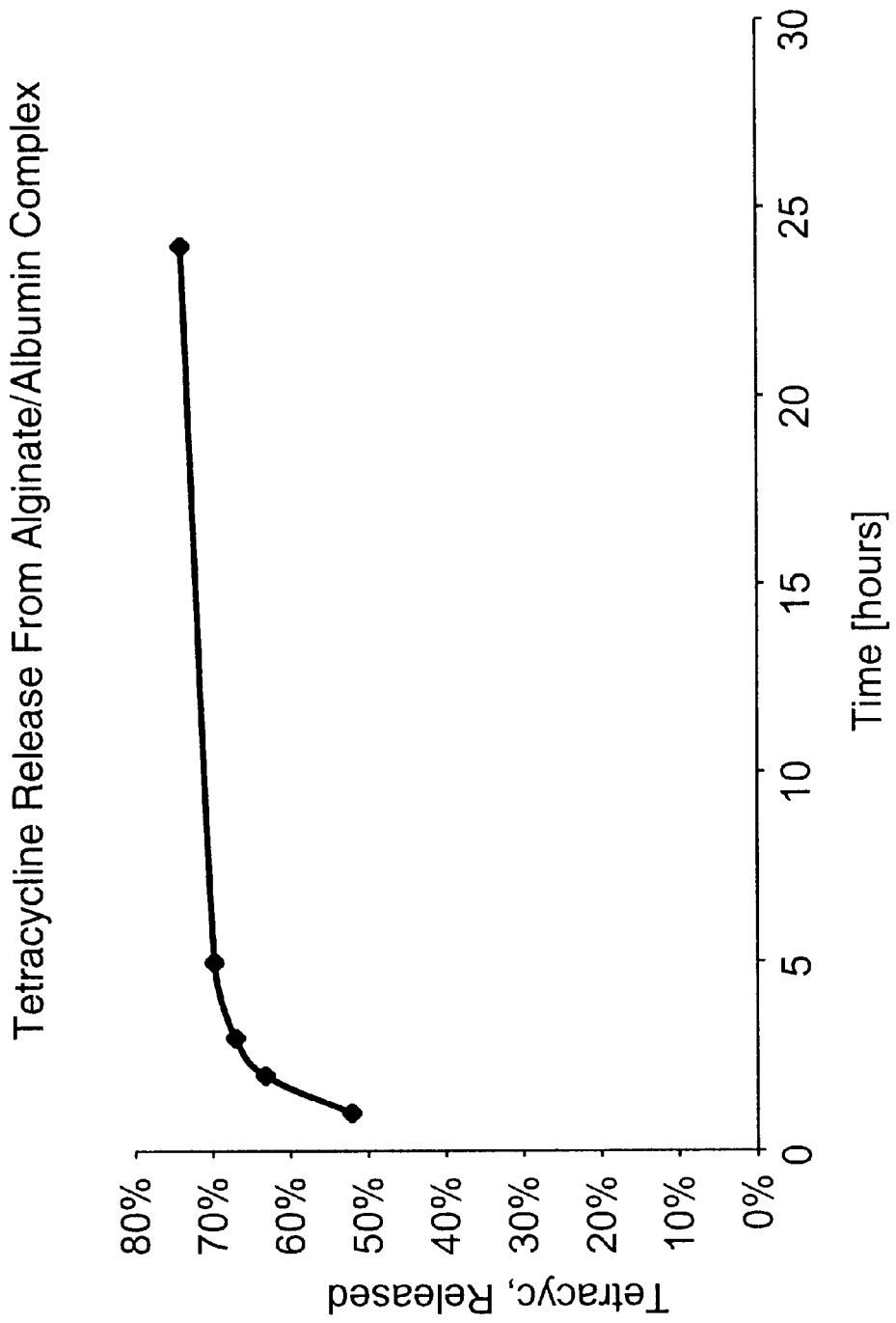
FIG. 2 shows the release of tetracycline from an alginate/drug complex, which was mixed into the albumin just prior to being crosslinked with the PEG-SS$_2$ crosslinker.

The data in FIG. 2 show that about 70% of the tetracycline was released over a 5 hr period. The amount of tetracycline collected was not corrected for losses due to tetracycline breakdown.

Example 3

Release of 5-Fluorouracil from a Plug Made with 5FU Mixed with the Crosslinker and Albumin 136 mg of $PEG-(SS)_2$ crosslinker was dissolved in 1 ml of a 1.04 mg/ml 5-Fluorouracil solution. This solution was then mixed into 1 ml of 30% albumin solution (see Example 2) already in a 5-ml form. The resulting hydrogel plug was removed from the form after 15 minutes and cut into three equal sized pieces (approximately 0.5 cm in thickness). Each piece was then placed into a vial and 4 ml of a PBS buffer (pH 7.4) added at sample time 0 ($t_0$). The vials were maintained at room temperature and were shaken continuously. At each sample time, the entire content of the vial was removed and replaced with 4 ml of fresh PBS. Samples were taken at 1 hr, 2 hr, 4 hr, and 8 hr. The 5-fluorouracil was analyzed as described in Example 1.

Figure 3:
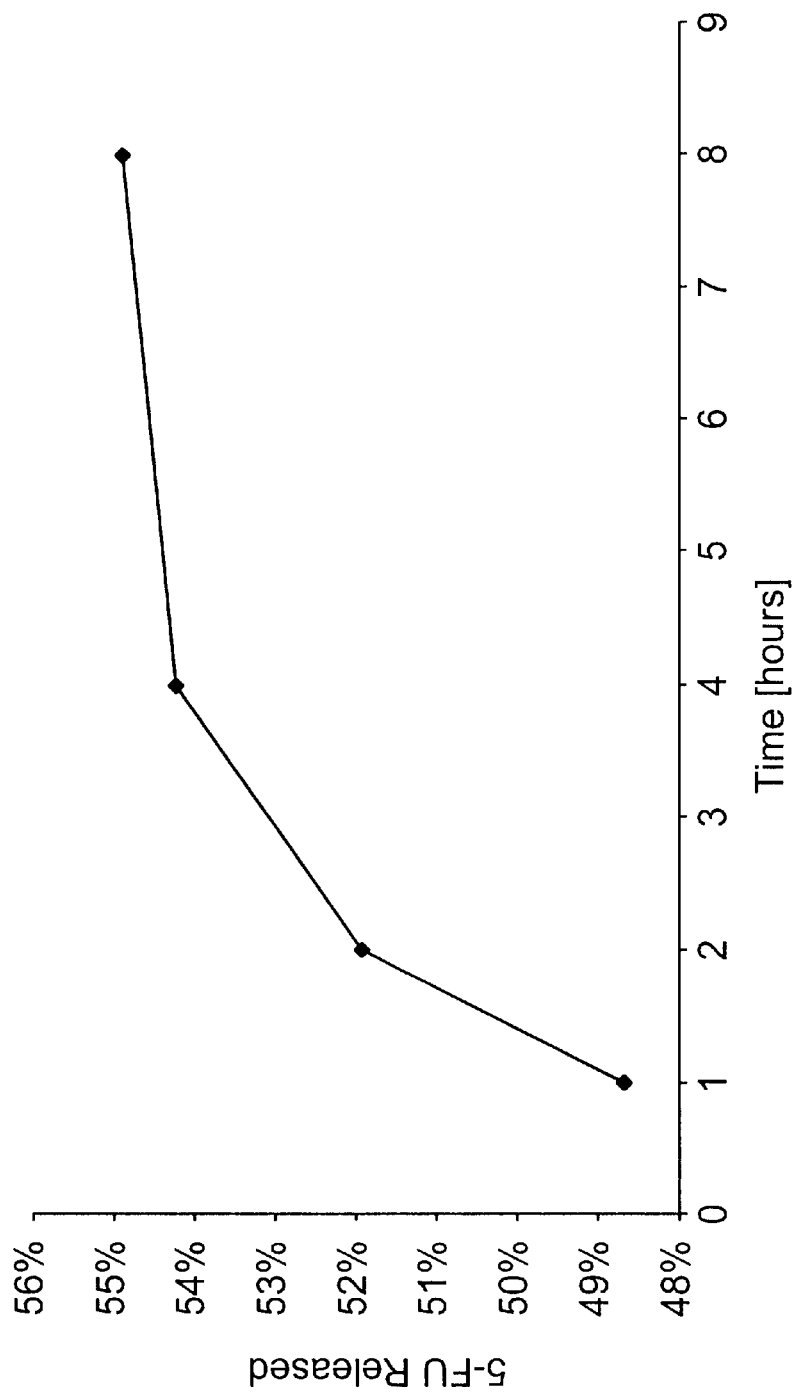
FIG. 3 shows the release of 5-FU from albumin/PEG-(SS)$_2$ plugs in which the 5-FU was added with the crosslinker during the manufacture of the plug.

The data in FIG. 3 show that about 55% of the 5-fluorouracil was released over an 8-hr period. The remainder of the 5FU was probably crosslinked into the polymer and would be released as the polymer disintegrated.

Example 4

Release of 5-Fluorouracil from Albumin Plugs Containing Alginic Acid without Added Calcium One milliliter of 1.04 mg/ml 5-fluorouracil was mixed with 30 mg of alginic acid. The pH of the mixture was brought to 6.8, and then placed into a vacuum desiccator with DRIERITE to dry for 24 hr. The resulting alginate/5FU film was ground up and mixed into the 30% albumin solution (see Example 2) just prior to being placed into the 5 ml syringe forms and crosslinked with an equivalent volume of PEG-$(SS)_2$ crosslinker (136 mg/ml). Each plug was placed into a separate vial, and 5 ml of phosphate buffered saline (PBS), at pH 7.4, was added at sample time 0 ($t_0$). The vials were maintained at room temperature and were shaken continuously. At each sample time, the entire content of the vial was removed and replaced with 5 ml of fresh PBS. Samples were taken at 1 hr, 2 hr, 3 hr, 4 hr, 5 hr, and 24 hr.

Figure 4:
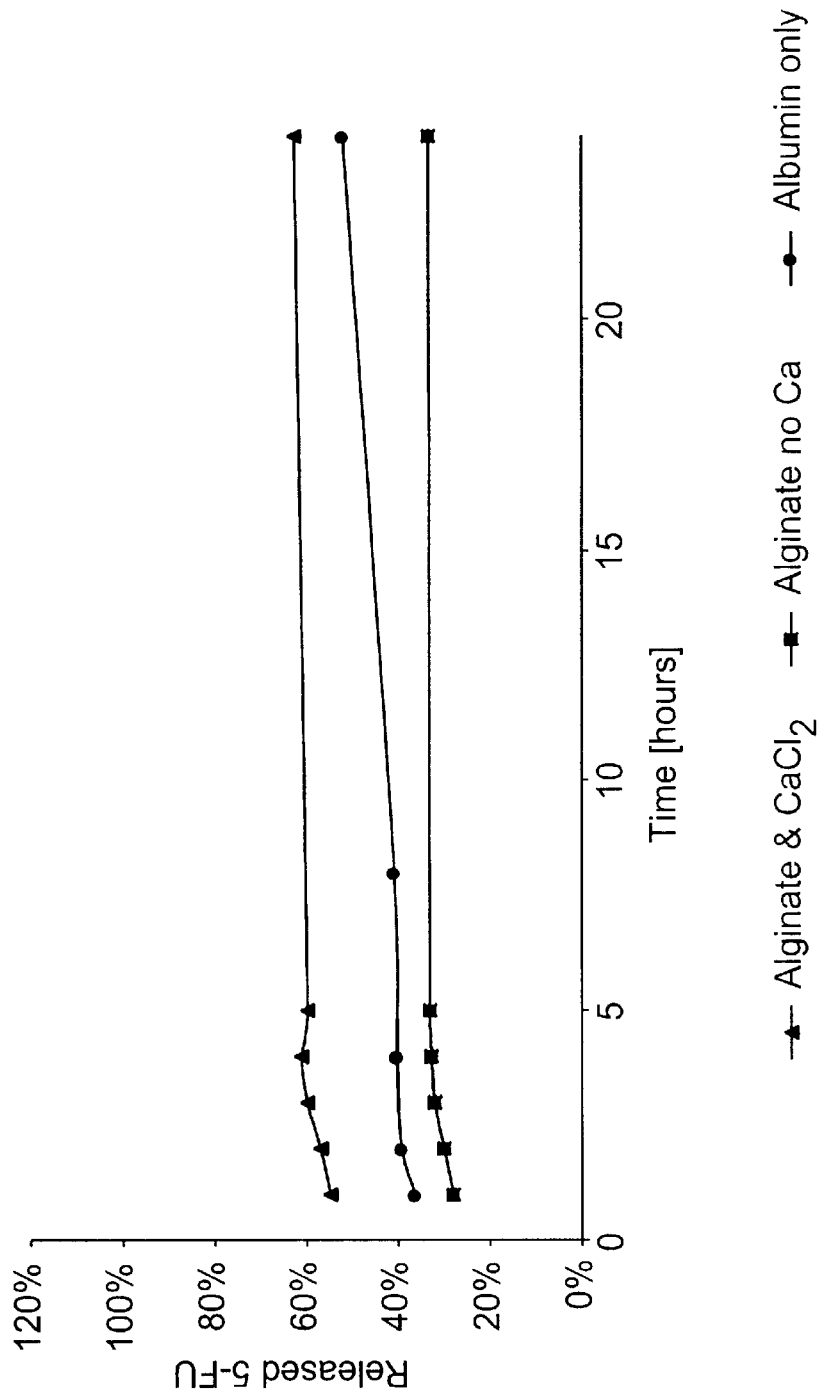
FIG. 4 shows the release of 5-FU from albumin/PEG-(SS)$_2$ plugs with calcium chloride added.

The 5FU was analyzed as in Example 1. The data in FIG. 4 show that about 40% of the 5FU was released over a 5-hr period.

Example 5

Release of 5-Fluorouracil from Albumin Plugs Containing Alginic Acid with Added Calcium One ml of 1.04 mg/ml 5-fluorouracil was mixed with 30 mg of alginic acid. The pH of the mixture was brought to 6.8, and 150 $\mu$l of a saturated calcium chloride/water solution was added to gel the alginate. The gel was divided into 3 approximately equal volumes and then placed into a vacuum desiccator with DRIERITE to dry for 24 hr. The resulting alginate/Ca/5FU films were ground up and mixed into the 30% albumin solution (see Example 2) just prior to being placed into the 5-ml forms and crosslinked with an equivalent volume of PEG-$(SS)_2$ crosslinker (136 mg/ml). Each plug was placed into a separate vial, and five mls of phosphate buffered saline (PBS), at pH 7.4, was added at sample time 0 ($t_0$). The vials were maintained at room temperature and were shaken continuously. At each sample time, the entire content of the vial was removed and replaced with 5 ml of fresh PBS. Samples were taken at 1 hr, 2 hr, 3 hr, 4 hr, 5 hr, and 24 hr.

The 5FU was analyzed as described in Example 1. The data in FIG. 4 shows that about 60% of the 5FU was released over a 5-hr period.

Example 6

Method for Making Biodegradable Beads

The beads were prepared from a two part liquid system. Part A was a sterile 29% solution of albumin (see Example 1) in isotonic (0.075 M) carbonate buffer (pH 9). Part B was a 260 mg/ml solution of PEG-$(SS)_2$, reconstituted in a sterile water solution just prior to use. Solutions A and B were mixed in equal volumes with a dual syringe system connected to a static mixing head. The beads were prepared by injecting the liquid into a Teflon mold 6 inches×4 inches×1 inch with 8-mm diameter holes. The injected mixture was allowed to cure for ten minutes in the 8-mm diameter holes. The beads were removed from the Teflon mold after ten minutes. The beads can be used in two different manners. In one case the hydrated beads can be used directly as they are removed from the Teflon mold. In another case the beads can be dehydrated after removal from the mold. Drying can be done under vacuum or in air or in other appropriate manners. It is important to note that a variety of geometries can be created other than spherical beads.

Example 7

In Vitro Release Studies of Vancomycin

Figure 5:
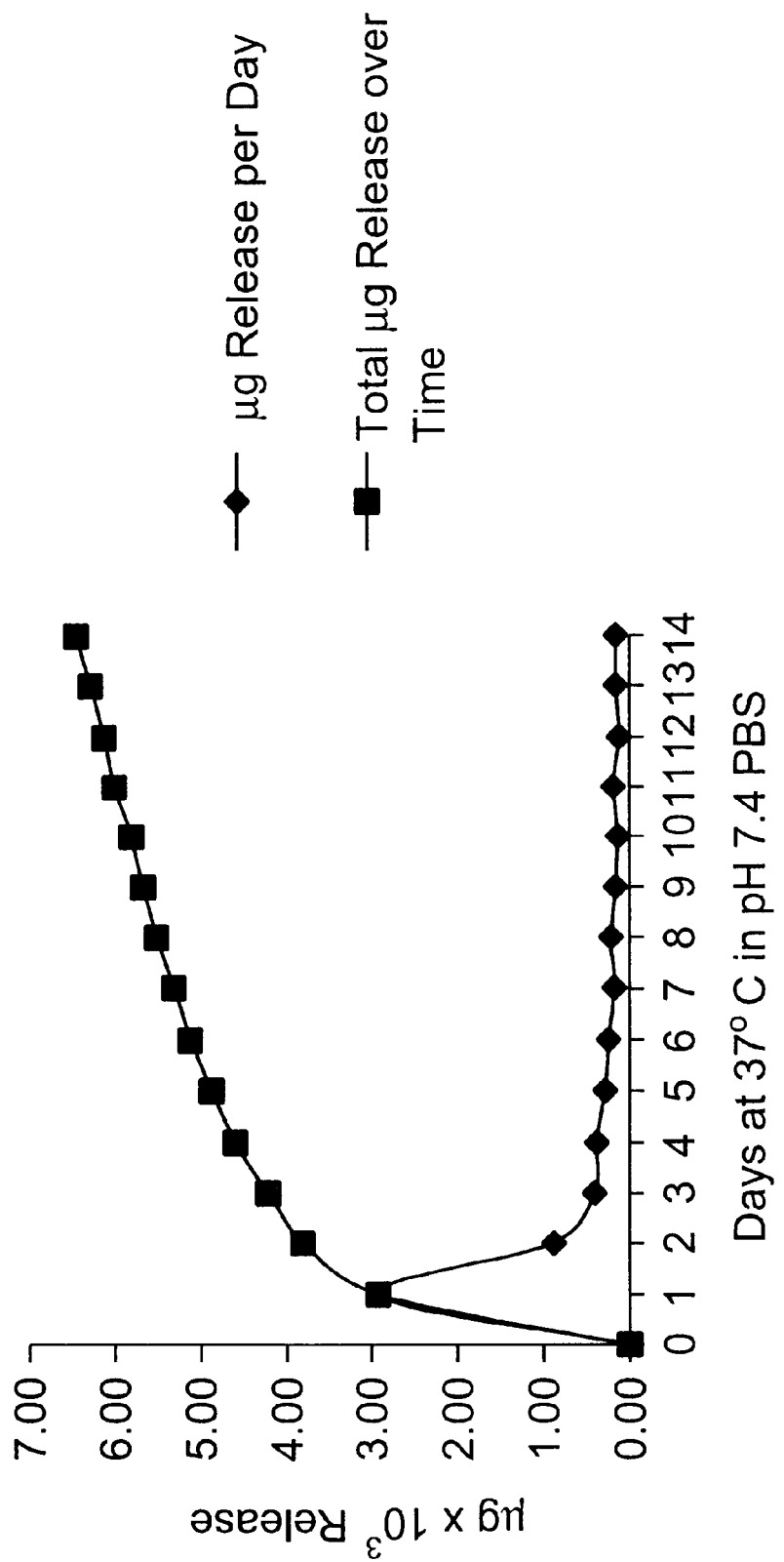
FIG. 5 shows the release of vancomycin from rehydrated albumin/PEG-(SS)$_2$ beads.
Figure 6:
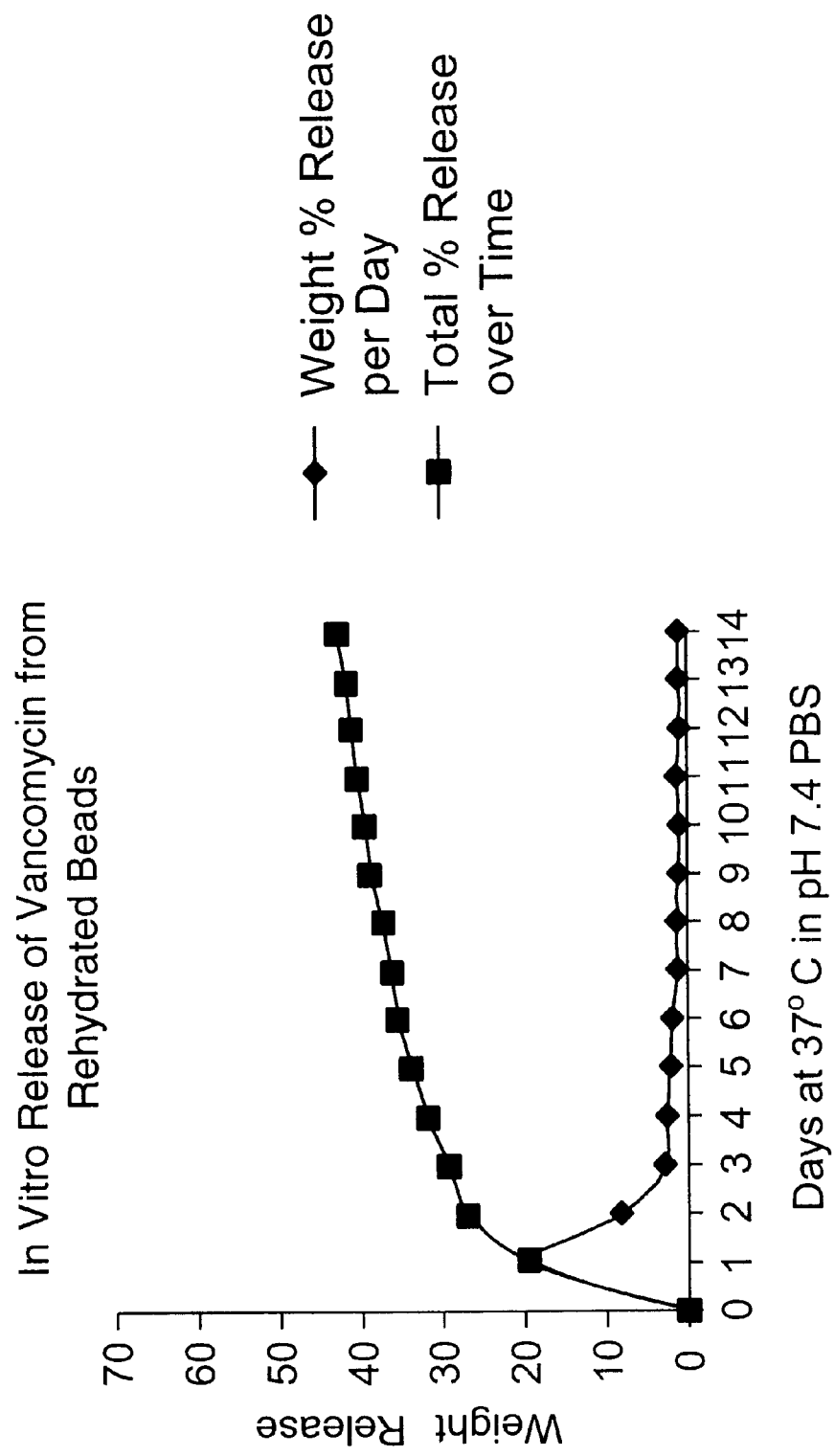
FIG. 6 shows the weight percent release of vancomycin from rehydrated albumin/PEG-(SS)$_2$ beads.

Two dehydrated beads made from Example 6 were placed in a 4-ml vial. Vancomycin (60 mg, Abbott Laboratories, North Chicago, Ill.) was dissolved in 2 ml of sterile water and added to the vial. The beads were soaked for 24 hours at room temperature. After 24 hours soaking, the beads were removed and placed in a 20-ml glass bottle with 5 ml of saline phosphate buffer pH 7.4. The vancomycin release rate was determined at 37° C. in a constant temperature water bath. The buffer was exchanged every 24 hours up to three weeks. These samples were analyzed for vancomycin by UV-Spectrophotometer (Beckman, DU640, Fullerton Calif.). Vancomycin was detectable at 282 nm. The results are shown in FIGS. 5 and 6.

Example 8

In Vitro Release of Cefazolin

Figure 7:
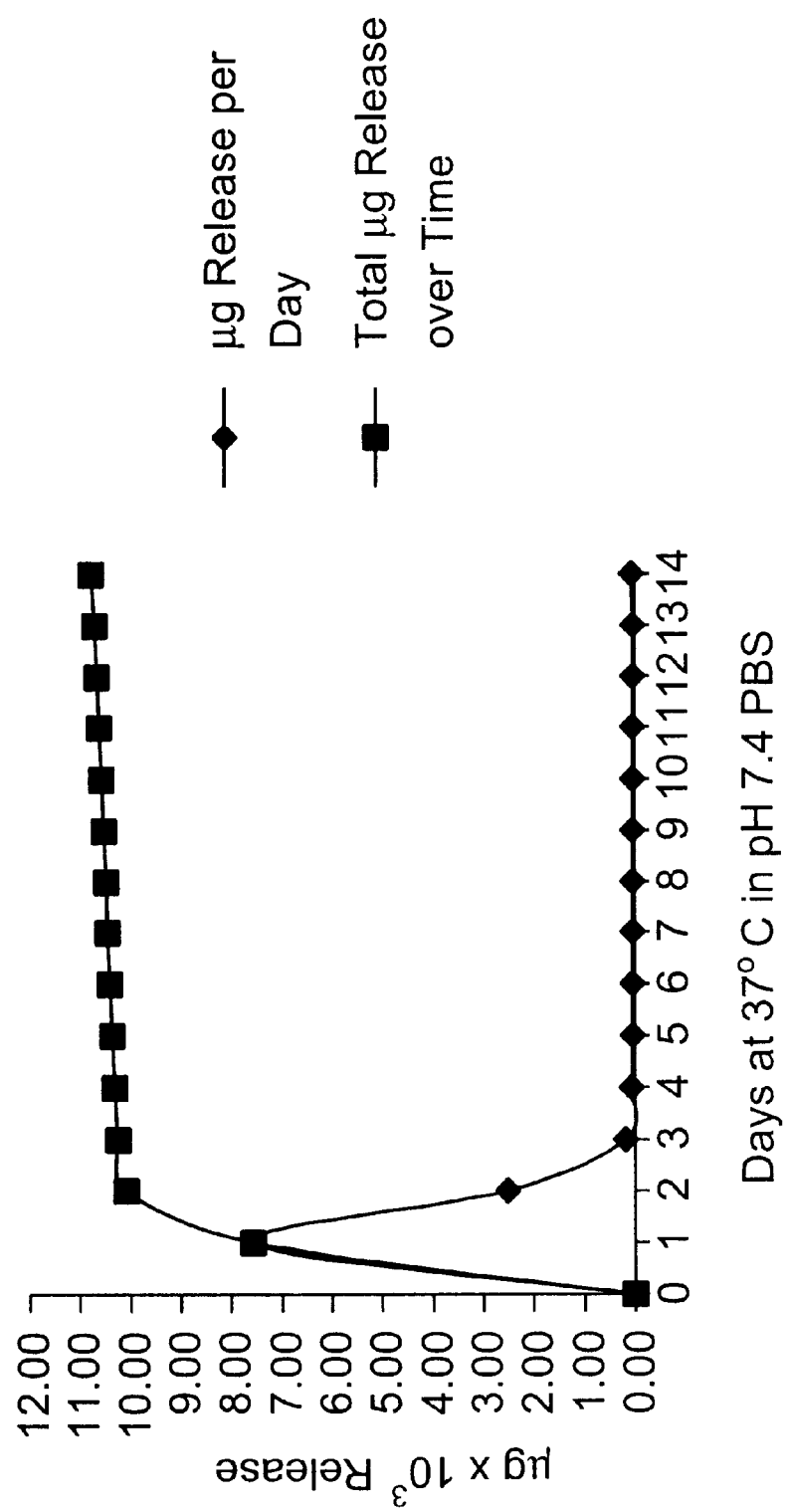
FIG. 7 shows the release of cefazolin from rehydrated albumin/PEG-(SS)$_2$ beads.
Figure 8:
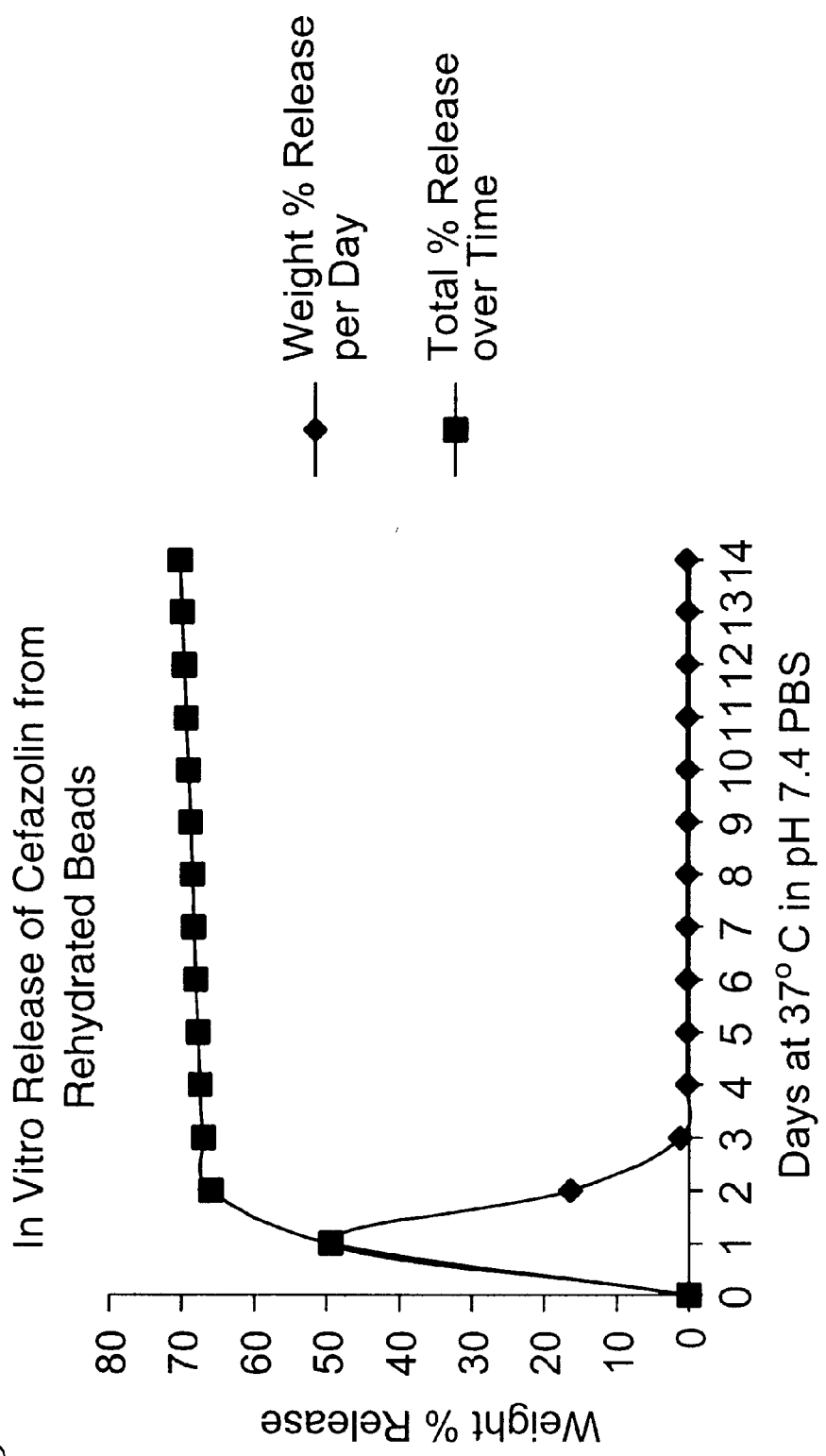
FIG. 8 shows the weight percent release of cefazolin from rehydrated albumin/PEG-(SS)$_2$ beads.

Two dehydrated beads made from Example 6 were placed in a 4-ml vial. Cefazolin (60 mg, Marsam Pharmaceuticals, Inc., Cherry Hill, N.J.) was dissolved in 2 ml of sterile water and added to the vial. The beads were soaked for 24 hours at room temperature. After 24 hours soaking, the beads were removed and placed in a 20-ml glass bottle with 5 ml of saline phosphate buffer pH 7.4. The cefazolin release rate was determined at 37° C. in a constant temperature water bath. The buffer was exchanged every 24 hours up to three weeks. These samples were analyzed for cefazolin by UV-Spectrophotometer (Beckman, DU640, Fullerton Calif.). Cefazolin absorbs at 272 nm. The results are shown in FIGS. 7 and 8.

Example 9

Water Uptake of Rehydrated Beads as a Function of Extent of Crosslinking and Solvent Volume Beads were made as in Example 6 except that several crosslinker formulations of PEG-$(SS)_2$ were used. Beads made with normal sealant (NS) formulation were made by mixing 130 mg PEG-$(SS)_2$ in 1 ml water and 1 ml of 29% albumin in pH 9.0 carbonate buffer. For beads with half the crosslinker concentration (NS*½), the beads contained 65 mg of PEG-$(SS)_2$ in 1 ml of water and 1 ml of 29% Albumin in pH 9.0 carbonate buffer. For beads with twice the crosslinker concentration (NS*2), the beads contained 260 mg of PEG-$(SS)_2$ in 1 ml of water and 1 ml of 29% albumin in a pH 9.0 carbonate buffer. For beads with triple the crosslinker concentration (NS*3), the beads contained 390 mg of PEG-(SS)$_2$ in 1 ml of water and 1 ml of 29% albumin in a pH 9.0 carbonate buffer. Three beads from each formulation were placed in a 20-ml pre-weighed vial. Three milliliters of water were weighed and added to the vial. The same experiment was repeated with six milliliters of water. Water uptake from the beads was measured at 2, 4, 6, 8, and 24 hours by taking the beads out and weighing the water in the vial. The results are shown in Table 1.

TABLE 1

Water uptake per Bead as a Function of Crosslinking and Volume

| | % Water Uptake per Bead | | | | | | |
|---|---|---|---|---|---|---|---|
| Time (Hrs) | (NS*1/2) 3 ml Water | (NS) 3 ml Water | (NS*2) 3 ml Water | (NS*3) 3 ml Water | (NS) 6 ml Water | (NS*2) 6 ml Water | (NS*3) 6 ml Water |
| 2 | 11.38 | 8.15 | 7.98 | 8.4 | 11.13 | 10.39 | 11.97 |
| 4 | 16.01 | 11.89 | 11.13 | 11.73 | 19.27 | 16.59 | 17.71 |
| 6 | | | | | 26.75 | 21.61 | 21.25 |
| 8 | 20.67 | 15.20 | 13.90 | 14.25 | 31.56 | 25.63 | 25.13 |
| 24 | 25.87 | 18.78 | 17.54 | 17.17 | 34.89 | 29.65 | 28.67 |

Example 10

Figure 9:
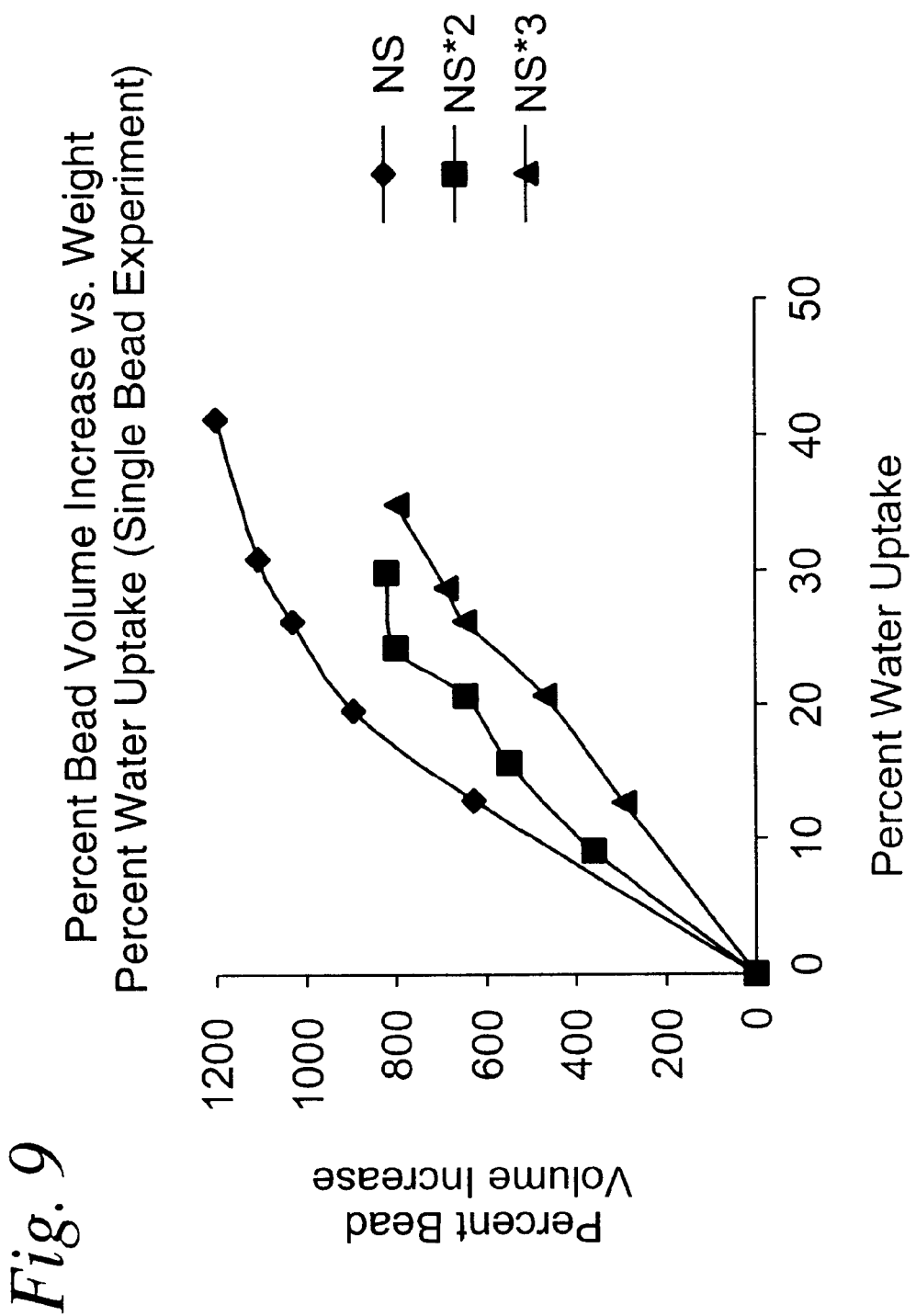
FIG. 9 shows the percent volume increase of polymer beads vs. the weight percent water uptake in a single bead experiment.

Water Uptake of Rehydrated Beads as a Function of Bead Diameter and Extent of Crosslinking Beads were made as in Example 6. Beads with normal, double, and triple crosslinker concentrations were made as described in Example 9. Three beads from each formulation were placed in a 20-ml pre-weighed vial. Six milliliters of water were weighed and added to the vial. Water uptake from bead and bead diameter was measured at 2, 4, 6, 8, and 24 hours by taking the beads out of the vials and weighing the water remaining in the vial. The experiment was repeated with one bead and two milliliters of water. The bead diameter was measured by using a Scherr-Tumico Optical Comparator (S.T. Industries). The results are shown in Table 2 for multiple beads and Table 3 for a single bead. Table 4 shows percent volume increase compared to the volume of dry beads as a function of time between single- and multiple-beads experiments as the dry beads rehydrated. FIG. 9 depicts this data with respect to water uptake for the 1-bead experiments. The 3 bead experiments yielded similar results.

TABLE 2

Water Uptake of Multiple Beads

| Time (Hrs) | (NS) 6 ml Water % Water Uptake per Bead | (NS*2) 6 ml Water % Water Uptake per Bead | (NS*3) 6 ml Water % Water Uptake per Bead | (NS) 6 ml Water Diameter per Bead (mm) | (NS*2) 6 ml Water Diameter per Bead (mm) | (NS*3) 6 ml Water Diameter per Bead (mm) |
|---|---|---|---|---|---|---|
| 0 | 0 | 0 | 0 | 4.35 | 4.65 | 4.92 |
| 2 | 11.13 | 10.39 | 11.97 | 6.99 | 6.98 | 6.78 |
| 4 | 19.27 | 16.59 | 17.71 | 8.08 | 7.84 | 7.64 |
| 6 | 26.75 | 21.61 | 21.25 | 8.73 | 8.0 | 8.62 |
| 8 | 31.56 | 25.63 | 25.13 | 9.05 | 8.8 | 8.86 |
| 24 | 34.89 | 29.65 | 28.67 | 9.42 | 8.91 | 9.13 |

TABLE 3

Water Uptake of Single Beads

| Time (Hrs) | (NS) 2 ml Water % Water Uptake per Bead | (NS*2) 2 ml Water % Water Uptake per Bead | (NS*3) 2 ml Water % Water Uptake per Bead | (NS) 2 ml Water Diameter per Bead (mm) | (NS*2) 2 ml Water Diameter per Bead (mm) | (NS*3) 2 ml Water Diameter per Bead (mm) |
|---|---|---|---|---|---|---|
| 0 | 0 | 0 | 0 | 4.07 | 4.66 | 4.93 |
| 2 | 12.87 | 9.10 | 12.63 | 6.9 | 6.52 | 6.53 |
| 4 | 19.57 | 15.68 | 20.71 | 8.11 | 7.5 | 7.5 |
| 6 | 26.26 | 20.74 | 26.26 | 8.73 | 8.0 | 8.47 |
| 8 | 33.47 | 24.28 | 28.79 | 9.07 | 8.8 | 8.7 |
| 24 | 41.19 | 29.84 | 34.85 | 9.5 | 8.91 | 9.30 |

TABLE 4

Water Uptake in Single/Multiple Bead Experiment

| Time (Hrs) | (NS) 2 ml Water (1 bead) % Vol. Inc. | (NS*2) 2 ml Water (1 bead) % Vol. Inc. | (NS*3) 2 ml Water (1 bead) % Vol. Inc. | (NS) 6 ml Water (3 bead) % Vol. Inc. | (NS*2) 6 ml Water (3 bead) % Vol. Inc. | (NS*3) 6 ml Water (3 bead) % Vol. Inc. |
|---|---|---|---|---|---|---|
| 2 | 387 | 174 | 132 | 315 | 329 | 163 |
| 4 | 691 | 317 | 252 | 542 | 379 | 275 |
| 6 | 887 | 406 | 407 | 710 | 540 | 440 |
| 8 | 1007 | 573 | 450 | 804 | 593 | 485 |
| 24 | 1172 | 599 | 571 | 918 | 611 | 541 |

Example 11

Preparation of Crosslinked Albumin Microspheres

Microspheres were prepared by a water-in-oil emulsion method according to U.S. Pat. No. 5,508,060, with various modifications. Human serum albumin (HSA) solution was used as taught in Example 8 of U.S. Pat. No. 5,583,114 (Barrows et al.), and bovine serum albumin (BSA), Fraction V, was purchased from Sigma Chemical Co. (St. Louis, Mo.). PEG-(SS)$_2$ was used as a crosslinking agent. In general, peanut oil (Nabisco Foods, Inc., East Hanover, N.J.) was stirred at a predetermined speed using a motor-driven three blade propeller-type stirrer (Motomatic, Electro-Craft, USA). Under constant stirring an aqueous solution of crosslinker mixed with an albumin solution was added dropwise with a hypodermic needle into the oil bath. In another variation, the crosslinker solution was added to the oil prior to dropwise addition of albumin solution. The albumin:crosslinker volume ratio was 1:1 and the concentrations of crosslinker used were 138 mg/ml and 276 mg/ml. The oil:water ratio was approximately 100:1 and a range of 300–500 ml of oil was used. After stirring for a predetermined period of time, the microspheres were collected and washed with ethyl acetate followed by filtration through a 0.44 μm or 1.1 μm cellulose or nylon filter.

Example 11A

The procedure of Example 11 was used to prepare microspheres with the following modifications. Human serum albumin (HSA) was used at 27% concentration and a pH of 9.4. The PEG-(SS)$_2$ solution was at 138 mg/ml concentration. The PEG-(SS)$_2$ solution was added to the oil and then the albumin solution was added dropwise to the stirred oil through a 27 gauge needle. The oil was stirred at 1000 rpm for 15 minutes using a three-blade propeller-type stirrer. After the stirring was stopped the solution was heated up to 85° C. and the microspheres were filtered and washed as in Example 11. During the heating of the solution when the temperature of the medium reached about 45° C., the crosslinked particles started to flocculate resulting in white flake formation from the mixture. The flocculated particles were removed and the microspheres were collected. A typical image analysis of the microspheres recovered from this process had a mean diameter of 4.22 µm and a size distribution within a range of 1.0 µm (microns) to 15 µm.

Example 11B

Microspheres were made by the same procedure used in Example 11A except that the stirring speed was 1300 rpm and no heat was applied to the solution after stirring. A typical image analysis of the microspheres recovered from this process had a mean diameter of 3.05 µm and a size distribution within a range of 1.0 µm to 10 µm.

Example 11C

Microspheres were made by the same procedure used in Example 11A except that the PEG-(SS)$_2$ crosslinker concentration was 276 mg/ml, the stirring speed was 1300 rpm, the stirring time was 20 minutes and no heat was applied to the solution after stirring. A typical image analysis of the microspheres recovered from this process had a mean diameter of 5.45 µm and a size distribution within a range of 0.5 µm to about 16 µm. These microspheres were used in the drug loading experiments in Example 12.

Example 11D

Microspheres were made by the same procedure used in Example 11A except that bovine serum albumin (BSA) was used at 15% solution and pH 9.17, stirring speed was 1500 rpm, stirring time was 20 minutes and no heat was applied to the solution after stirring. A typical image analysis of the microspheres recovered from this process had a mean diameter of 2.42 µm and a size distribution within a range of 1.0 µm to 6.0 µm.

Example 12

In Situ Drug Loading of Microspheres with Tetracycline

Microspheres were prepared in the presence of tetracycline hydrochloride according to the method of Example 11C by mixing 2 ml of HSA solution with an equal volume of a crosslinker solution containing the drug in an oil bath. Briefly, the crosslinker solution was prepared by adding 552 mg of PEG-(SS)$_2$ crosslinker into 2 ml of tetracycline solution (10 mg/ml). The drug-containing PEG-(SS)$_2$ solution was added into the oil while stirring at 1300 rpm. After allowing sufficient time for the aqueous solution to form a stable emulsion, 2 ml of human serum albumin (27%, pH 9.4) was added dropwise and the emulsion was stirred for 20 minutes. After washing with ethyl acetate, the particles were presented as a well-separated fine powder. The image analysis showed the particles to be well separated and small in size.

Example 13

In Vitro Evaluation of Drug Release

In vitro drug release studies were carried out by placing microspheres (see Example 11A) in a vessel of an extended release tester (BIO-DIS, VanKel, Edison, N.J.). The vessel was immersed into a 200-ml glass beaker containing 100 ml of phosphate-buffered saline (PBS, pH 7.4) at an agitation rate of 3 dips per minute, with an initial 5 second delay. The bath temperature was electronically maintained at 37° C. throughout the release study. At predetermined times, one ml of sample was taken out, followed by an addition of fresh solution into the PBS reservoir. The sample solution was filtered through a 0.22 m COSTAR syringe filter (Corning, Corning, N.Y.) to exclude any particulate. Quantitative determinations of tetracycline hydrochloride were made using the HPLC method with spectrometric UV detection. The apparatus used consisted of an injector (Shimadzu Model Sil-9A, Shimadzu, Columbia, Md.), a solvent delivery system (Waters 625 LC, Millipore Corporation, Milford, Mass.), a multi-wavelength detector (Waters 490E, Millipore Corporation, Milford, Mass.) and an integrator (Waters Millennium, Millipore Corporation, Milford, Mass.). The drug containing solutions (20 µl–150 µl, adjusted so as to be in linear detection range) were injected into the Beckman reverse phase C-18 column (5 µm×4.6 mm×25 cm (Beckman, USA). The mobile phase was an 80/20 mixture of water and acetonitrile containing 0.1% trifluoroacetic acid. The flow rate was 1.0 ml/minute and the UV wavelength used was 275 nm. The drug concentration was determined by comparing the area under the drug peak to that derived from a standard curve. Each sample was analyzed at least twice, and the average total drug released was calculated.

Figure 10:
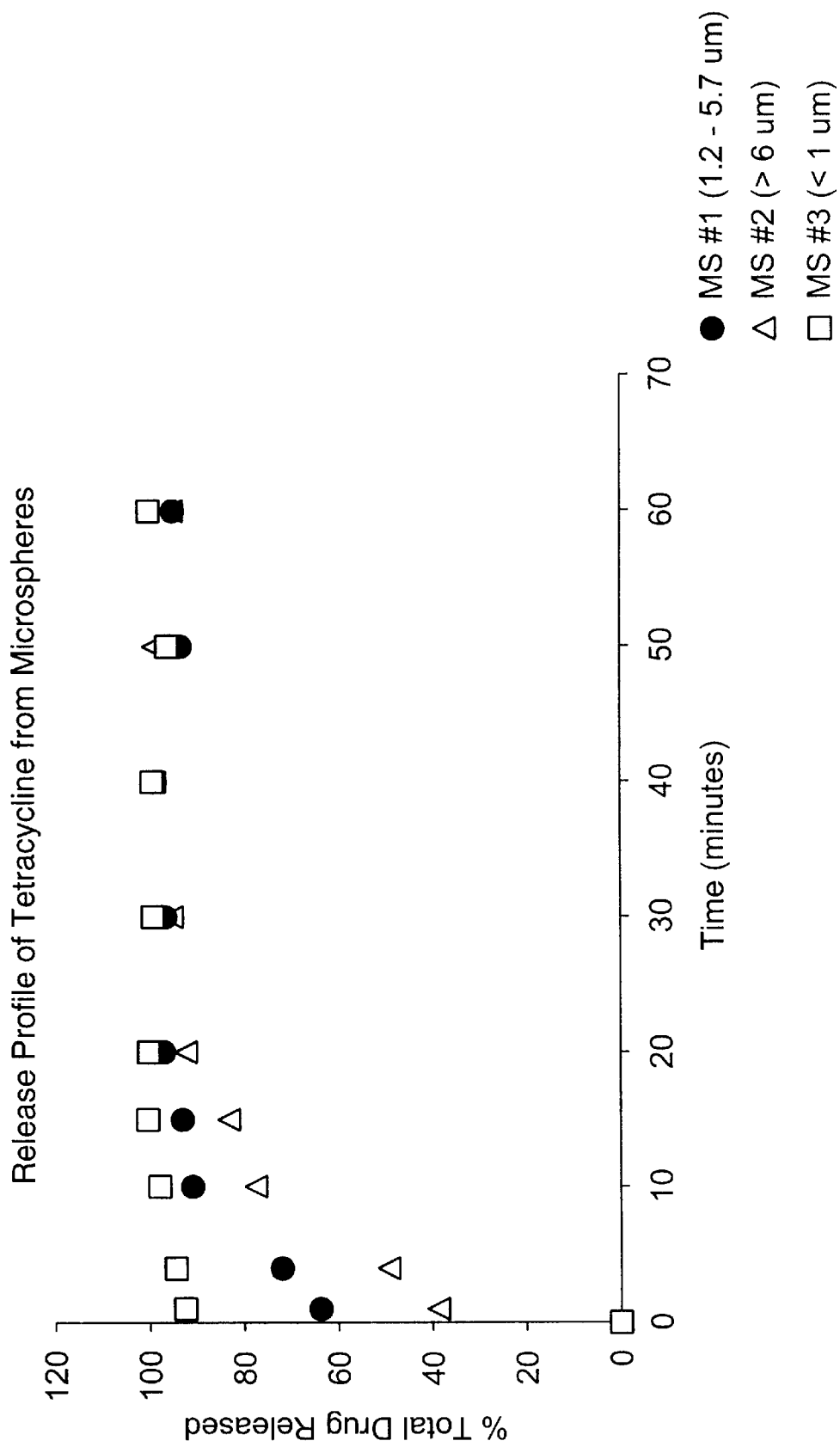
FIG. 10 shows the release profiles of tetracycline from microspheres.

FIG. 10 shows the release profiles of tetracycline hydrochloride from the microspheres with three different size ranges. The sizing was carried out by a differential sedimentation method. An initial burst release was observed in all three preparations. However, there was a significant influence of particle size on the burst effect. The initial drug flux from the microspheres was decreased as the particle size increased, indicating that the initial burst phase was mainly dependent on the surface area of microspheres.

Example 14

Release of Cefazolin from Albumin Polymer Plugs made with 4-armPEG Crosslinker

Figure 11:
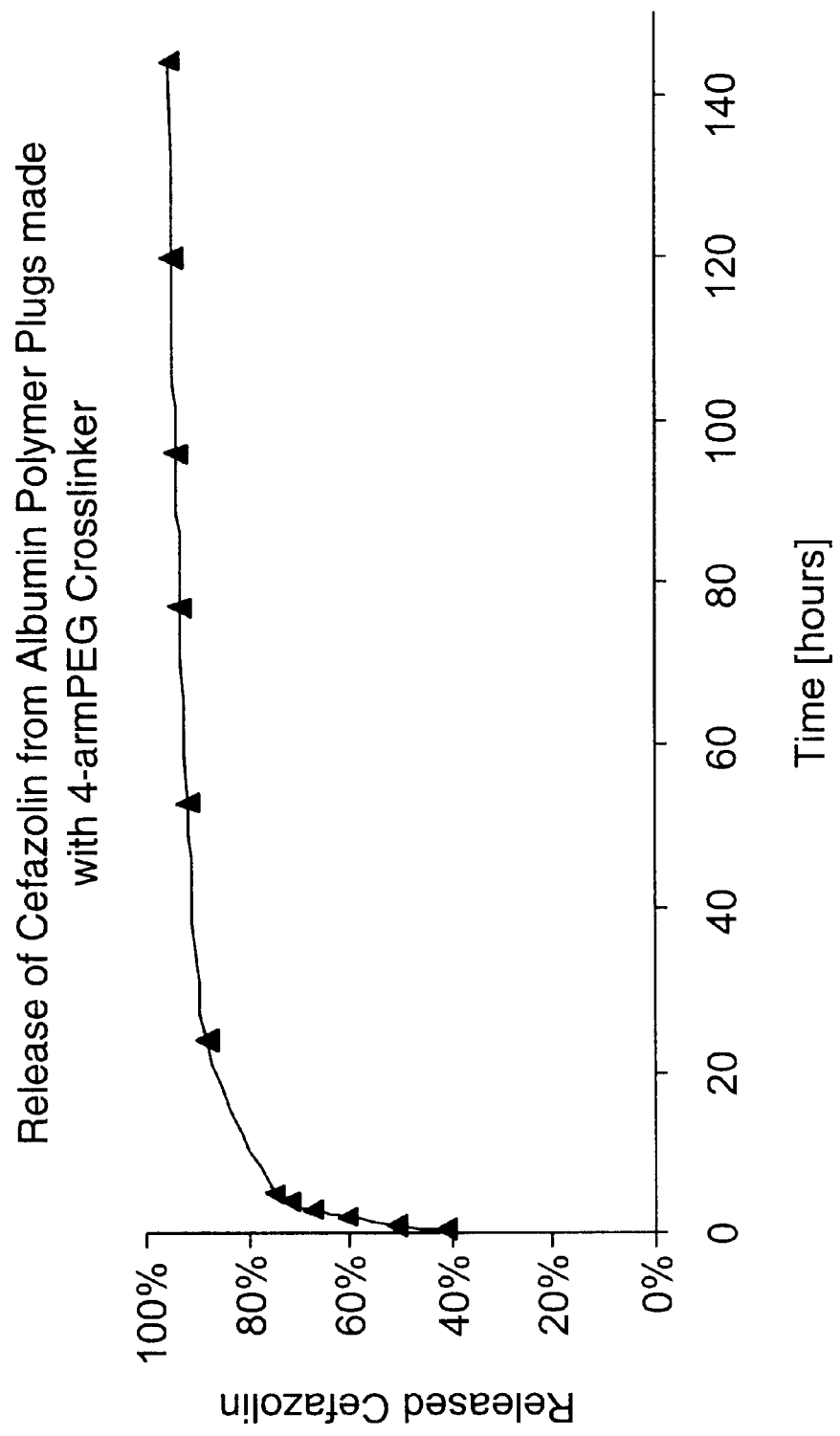
FIG. 11 shows the release of cefazolin from albumin/4-arm PEG plugs.

Two polymer plugs were preformed from 0.5 ml of 30% albumin solution (Procedure B) and 0.5 ml of 110 mg/ml 4-arm-N-hydroxysuccinimidyl ester of poly(ethylene glycol)-succinate crosslinker (Shearwater Polymers, Inc., Huntsville, Ala.). Approximately 10 mg of sodium cefazolin (Sigma Chemical. Co., St. Louis, Mo.) was dissolved in the albumin before the crosslinker was added to form the cylindrical plugs. Each formed plug was placed into a separate vial, and 8 mls of phosphate buffered saline (PBS) at pH 7.4 was added at sample time ($t_0$). The vials were maintained at room temperature and were shaken continuously. At each sample time, the entire content of the vial was removed and replaced with eight ml of fresh PBS. Samples were taken at 0.25, 0.5, 1, 2, 3, 4, 5, and 24 hours and approximately every 24 hours thereafter up to 144 hours. The data in FIG. 11 show that approximately 67% of the cefazolin was released over the first 5-hour time period and 95.6% of the total cefazolin was released over 144 hours.

Cefazolin was analyzed by high-pressure liquid chromatography, following the method of Liang et al, *J. Chromatog. B.,* 656, 45–465 (1994). The column was a Waters C-18 (3.9×300 mm) column sold under the tradename MICROBONDAPAK and the column temperature was maintained at 25° C. The mobile phase consisted of 0.02M sodium phosphate buffer (pH=5.0 and methanol (77:23). The wavelength used for detection was 270 nm and the column flow rate was 1.0 ml/min.

Example 15

Release of TGF-β1 from Biodegradable Preformed Albumin Beads

The beads were prepared according to the method described in Example 6 with the following variations: two beads were prepared exactly as described in Example 6 and used in their hydrated form (beads NS1 and NS2); two beads were prepared exactly as described in Example 6, dehydrated, and rehydrated in water (beads NS3 and NS4); two beads were prepared with the addition of 20 μl of 3.75 μg/ml human recombinant transforming growth factor β1 (TGF-β1, Gibco BRL, Rockville, Md.) to Part B of Example 6 to obtain a final concentration of 25 ng of TGF-β1 per bead and used in their hydrated form (beads NS5 and NS6); two beads were prepared exactly as described in Example 6, dehydrated, and rehydrated for 4 hours in 2 ml of a solution of 50 ng/ml of TGF-β1 (since 25% uptake was seen in 4 hours, 25 ng out of 100 ng were incorporated in each bead NS7 and NS8); two beads were prepared with Part A of Example 6 consisting of a sterile 23% solution of albumin (Procedure B) in isotonic (0.075 M) carbonate buffer (pH 8.66) and Part B consisting of a 65 mg/ml solution of PEG(SS)$_2$ (see Example 1) reconstituted in sterile water just prior to use (beads FS1 and FS2); two beads were prepared with Part A of Example 6 consisting of a sterile 23% solution of albumin in isotonic (0.075 M) carbonate buffer (pH 8.66) and Part B consisting of a 65 mg/ml solution of PEG-(SS)$_2$ (see Example 1) reconstituted in sterile water to which 20 μl of 3.75 μg/ml human recombinant TGF-β1 was added (beads FS3 and FS4).

All beads were put in 4 ml of modified Eagle's Minimum Essential Cell Culture Medium (American Type Culture Collection, Manassas, Va.) containing 10% Fetal Bovine Serum (American Type Culture Collection, Manassas, Va.) and penicillin/streptomycin 100 U/ml (Gibco BRL, Rockville, Md.) in individual wells of a 12-well petri plate (Fisher Scientific, Pittsburgh, Pa.). The plate was placed in a cell culture incubator (37° C., 5% CO$_2$) for the duration of the experiment. Samples were taken over time (starting with t=0), replacing the total volume of culture medium at each time point, until complete degradation of the beads. The medium at each time point was collected in a cryovial and stored at −20° C. Time points were 0, 24 hours, 48 h, 72 h, 96 h, 120 h, 144 h, 168 h, 192 h, 216 h, 240 h, 264 h, 289 h, and 330 h for NS beads and 0, 24 h, 48 h, 72 h, 96 h, and 120 h for FS beads.

All samples of culture medium were then assayed with an enzyme-linked immunosorbent assay (ELISA) for the determination of the concentration of TGF-β1 (QUANTIKINE for human TGF-β1, R&D Systems, Minneapolis, Minn.) according to the instructions of the manufacturer. Samples did not require activation since the TGF-β1 measured was active from a commercial source and not generated by cells in culture. An additional dose-response curve was generated with the same source of TGF-β1 used in the fabrication of the beads and results were calculated according to this latter dose-response curve.

Figure 12:
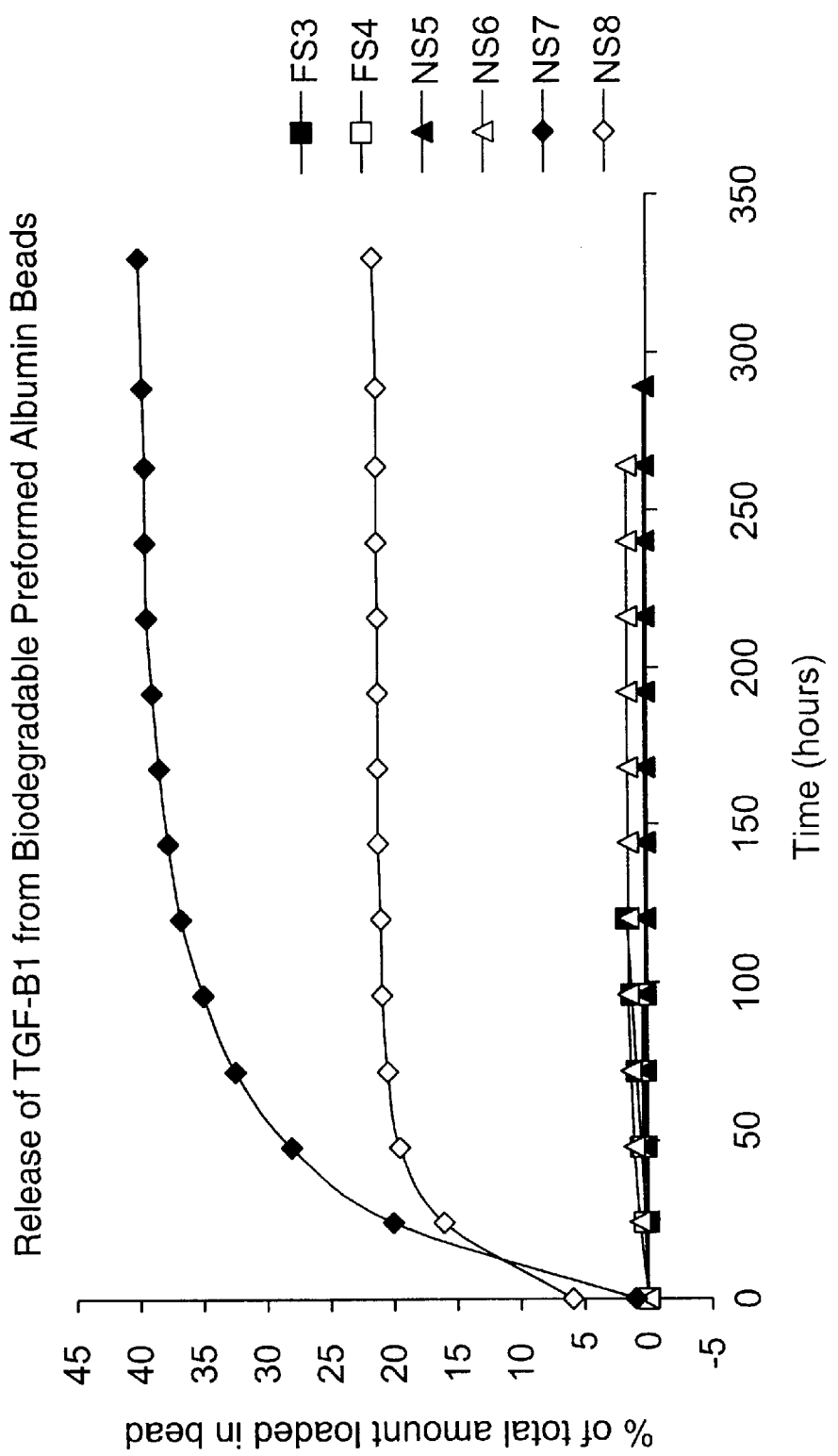
FIG. 12 shows the percentage of TGF-β1 released from various beads.

The results from FIG. 12 show that incorporation of the growth factor in a solution used for the rehydration of beads (NS7, NS8) leads to a release of up to 40% of the incorporated growth factor in 2–6 days. The incorporation of TGF-β1 with the crosslinker (NS5, NS6, FS3, FS4) does not lead to release of significant amounts of TGF from the beads. The control beads (NS1, NS2, NS3, NS4, FS1, FS2, without TGF-β1) were tested and did not interfere with the assay.

It will be readily understood by those skilled in the art that the foregoing description has been for purposes of illustration only and that a variety of embodiments can be envisioned without departing from the scope of the invention.

Therefore, it is intended that the invention not be limited except by the claims. The entirety of each patent, patent document, and publication cited herein is incorporated herein by reference as if each was individually incorporated.

What is claimed is:

1. A preformed object for delivering an active agent to a subject, the preformed object being self-supporting and at least partially desolvated crosslinked protein having a crosslinking agent of the formula:

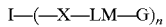

wherein:
X is a difunctional polyoxyethylene chain portion or a bond;
LM is a difunctional linking moiety represented by the formulas —C(O)—, —(CH$_2$)$_b$C(O)— where b is an integer from 1 to 5, —C(O)—(CH$_2$)$_c$—(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments;
G is a leaving group selected from the group of N-oxysuccinimidyl, N-oxymaleimidyl, N-oxyphthalimidyl, nitrophenoxyl, N-oxyimidazolyl, and tresyl;
I is a multifunctional linking moiety derived from a multinucleophilic compound; and
n is an integer from 2 to 10;
with the proviso that when X is a difunctional polyoxyethylene chain portion —X—I—X— is PEG, which is a diradical fragment represented by the formula:

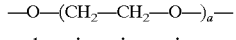

wherein a is an integer from 20 to 300.

2. The preformed object of claim 1 wherein the crosslinked protein comprises crosslinked serum albumin.

3. The preformed object of claim 2 wherein the crosslinked serum albumin comprises crosslinked human serum albumin.

4. The preformed object of claim 1 wherein G is N-oxysuccinimidyl.

5. The preformed object of claim 1 further comprising an active agent incorporated therein.

6. The preformed object of claim 1 wherein the active agent is selected from:
an antibacterial agent, a growth factor, an anticancer agent, a local anesthetic, an antiseptic, a hormone, an antiviral agent, a narcotic antagonist, an immune response modifier, an ocular drug, a vaccine, metabolic precursors thereof, and mixtures thereof.

7. The preformed object of claim 1 dispersed in a secondary biodegradable polymeric matrix.

8. The preformed object of claim 1 which is in the form of a sheet, ball, bead, sphere, plug, fiber, ribbon, or wedge.

9. The preformed object of claim 1 which is in the form of a bead having a diameter of greater than about 1 millimeter.

10. The preformed object of claim 1 which is in the form of a microsphere having a diameter of about 1 micron to about 1000 microns.

11. A preformed object for delivering an active agent to a subject the preformed object being self-supporting and comprising an active agent dispersed within a crosslinked protein having a crosslinking agent of the formula:

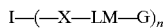

wherein:
X is a difunctional polyoxyethylene chain portion or a bond;
LM is a difunctional linking moiety represented by the formulas —C(O)—, —(CH$_2$)$_b$C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments;
G is a leaving group selected from the group of N-oxysuccinimidyl, N-oxymaleimidyl, N-oxyphthalimidyl, nitrophenoxyl, N-oxyimidazolyl, and tresyl;
I is a multifunctional linking moiety derived from a multinucleophilic compound; and
n is an integer from 2 to 10;
with the proviso that when X is a difunctional polyoxyethylene chain portion —X—I—X— is PEG, which is a diradical fragment represented by the formula:

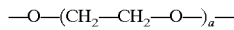

wherein a is an integer from 20 to 300.

12. The preformed object of claim 11 wherein the crosslinked protein comprises crosslinked serum albumin.

13. The preformed object of claim 12 wherein the crosslinked serum albumin comprises crosslinked human serum albumin.

14. The preformed object of claim 11 wherein G is N-oxysuccinimidyl.

15. The preformed object of claim 11 which is at least partially dehydrated.

16. The preformed object of claim 11 wherein the active agent is selected from:
an antibacterial agent, a growth factor, an anticancer agent, a local anesthetic, an antiseptic, a hormone, an antiviral agent, a narcotic antagonist, an immune response modifier, an ocular drug, a vaccine, metabolic precursors thereof, and mixtures thereof.

17. The preformed object of claim 11 dispersed in a secondary biodegradable polymeric matrix.

18. The preformed object of claim 11 which is in the form of a sheet, ball, bead, sphere, plug, fiber, ribbon, or wedge.

19. The preformed object of claim 11 which is in the form of a bead having a diameter of greater than about 1 millimeter.

20. The preformed object of claim 11 which is in the form of a microsphere having a diameter of about 1 micron to about 1000 microns.

21. The preformed object of claim 11 which is a ball-shaped object that is at least partially dehydrated.

22. A method of forming a preformed object for delivering an agent, the method comprising:
providing a first aqueous mixture comprising a protein;
providing a second aqueous mixture comprising a crosslinking agent of the formula:

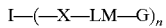

wherein:
X is a difunctional polyoxyethylene chain portion or a bond,
LM is a difunctional linking moiety represented by the formulas —C(O)—, —(CH$_2$)$_b$C(O)— where b is an integer from 1 to 5, —C(O)—(CH$_2$)$_c$—C(O)— where c is an integer from 2 to 10 and where the aliphatic portion of the radical may be saturated or unsaturated, —C(O)—O—(CH$_2$)$_d$—O—C(O)— where d is an integer from 2 to 10, or an oligomeric diradical represented by the formulas —R—C(O)—, —R—C(O)—(CH$_2$)$_c$—C(O)—, or —R—C(O)—O—(CH$_2$)$_d$—O—C(O)— where c is an integer from 2 to 10, d is an integer from 2 to 10, and R is a polymer or copolymer having 1 to 10 monomeric lactide, glycolide, trimethylene carbonate, caprolactone or p-dioxanone fragments,
G is a leaving group selected from the group of N-oxysuccinimidyl, N-oxymaleimidyl, N-oxyphthalimidyl, nitrophenoxyl, N-oxyimidazolyl, and tresyl,
I is a multifunctional linking moiety derived from a multinucleophilic compound, and
n is an integer from 2 to 10,
with the proviso that when X is a difunctional polyoxyethylene chain portion —X—I—X— is PEG, which is a diradical fragment represented by the formula:

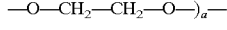

wherein a is an integer from 20 to 300;
combining the first and second aqueous mixtures and forming an article; and
exposing the article to conditions effective to crosslink the protein with the crosslinking agent to form a self-supporting preformed object.

23. A method of delivering an active agent to a subject, the method comprising contacting a subject with the preformed object of claim 5.

24. The method of claim 23 wherein contacting comprises implanting the preformed object into the subject.

25. The method of claim 23 wherein contacting comprises packing a plurality of the preformed objects into a tissue void within the subject.

26. A method of delivering an active agent to a subject, the method comprising contacting a subject with the preformed object of claim 11.

27. The method of claim 26 wherein contacting comprises implanting the preformed object into the subject.

28. The method of claim 26 wherein contacting comprises packing a plurality of the preformed objects into a tissue void within the subject.

* * * * *

UNITED STATES PATENT AND TRADEMARK OFFICE
CERTIFICATE OF CORRECTION

PATENT NO. : 6,576,263 B2  
DATED : June 10, 2003  
INVENTOR(S) : Truong, Myhanh T.

Page 1 of 1

It is certified that error appears in the above-identified patent and that said Letters Patent is hereby corrected as shown below:

Title page,
Item [57], ABSTRACT, delete the word "for" and insert in place thereof -- to --;

Column 9,
Lines 12-13, "Synthesis of Polyethylene Glycol Disuccinimidyl" should be listed together on line 13 as a heading;

Column 10,
Line 18, "Ana" should be -- Analysis --;

Column 18,
Line 25, "-C(O)-(CH$_2$)$_c$-(O)-" should be -- -C(O)-(CH$_2$)$_c$-C(O)- --;

Column 20,
Line 43, "-O-CH$_2$-CH$_2$-O-)$_a$" should read -- -O-(CH$_2$-CH$_2$-O-)$_a$ --.

Signed and Sealed this

Second Day of March, 2004

JON W. DUDAS
*Acting Director of the United States Patent and Trademark Office*